United States Patent
Shultz et al.

(10) Patent No.: US 10,021,861 B2
(45) Date of Patent: *Jul. 17, 2018

(54) GENETICALLY MODIFIED NON-HUMAN ANIMALS AND METHODS RELATING TO INNATE IMMUNE SYSTEM RESPONSE DETECTION

(71) Applicants: The Jackson Laboratory, Bar Harbor, ME (US); University of Massachusetts, Boston, MA (US)

(72) Inventors: Leonard D. Shultz, Bar Harbor, ME (US); Dale L. Greiner, Hubbardston, MA (US); Michael A. Brehm, Dudley, MA (US)

(73) Assignees: The Jackson Laboratory, Bar Harbor, ME (US); University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,165

(22) Filed: Aug. 15, 2016

(65) Prior Publication Data
US 2016/0345548 A1 Dec. 1, 2016

Related U.S. Application Data

(63) Continuation of application No. 14/511,793, filed on Oct. 10, 2014, now Pat. No. 9,414,576.

(60) Provisional application No. 61/889,804, filed on Oct. 11, 2013.

(51) Int. Cl.
| | | |
|---|---|---|
| *A01K 67/00* | (2006.01) | |
| *G01N 33/00* | (2006.01) | |
| *A01K 67/027* | (2006.01) | |
| *G01N 33/50* | (2006.01) | |

(52) U.S. Cl.
CPC ...... *A01K 67/0276* (2013.01); *A01K 67/0271* (2013.01); *G01N 33/5023* (2013.01); *G01N 33/5088* (2013.01); *A01K 2207/12* (2013.01); *A01K 2207/20* (2013.01); *A01K 2217/056* (2013.01); *A01K 2217/15* (2013.01); *A01K 2227/105* (2013.01); *A01K 2267/03* (2013.01); *A01K 2267/0387* (2013.01); *G01N 2333/70596* (2013.01)

(58) Field of Classification Search
None
See application file for complete search history.

(56) References Cited

PUBLICATIONS

Gülden, E. et al., Toll-Like Receptor 4 Deficiency Accelerates the Development of Insulin-Deficient Diabetes in Non-Obese Diabetic Mice, PLOS One, 8(9): e75385, pp. 1-8, Sep. 2013.
Li, Y. et al., Induction of Functional Human Macrophages from Bone Marrow Promonocytes by M-CSF in Humanized Mice, The Journal of Immunology, 191: 3192-99, Aug. 9, 2013.
Lu, Y. et al., LPS/TLR4 signal transduction pathway, Cytokine, 42: 145-51, 2008.
Rathinam, C. et al., Efficient differentiation and function of human macrophages in humanized CSF-1 mice, Blood, 118(11): 3119-28, Sep. 15, 2011.
Wen, L. et al., Innate immunity and intestinal microbiota in the development of Type 1 diabetes, Nature, 455: 1109-13, Oct. 23, 2008.
Xu et al, Cell Transplantation, vol. 22. pp. 2367-2380, Online prepub date: Nov. 8, 2012.
Hoshino et al., The Journal of Immunology, 1999. vol. 162: 3749-3752.
Sigmund, C.D. 2000. Arterioscler Thromb Vasc Biol. 20:1425-1429.
Wall, R.J. 1996. Theriogenology 45:57-68.
Bradley et al., paragraph bridging pp. 537-538.
Mullins et al.,1996, Clin. Invest. vol. 97, No. 7, 1557-1560.
Campbell et al., Theriogenology, vol. 47, pp. 69-72, 1997.

*Primary Examiner* — Celine Qian
(74) *Attorney, Agent, or Firm* — Dinsmore & Shohl LLP

(57) ABSTRACT

Described herein are immunodeficient non-human animals lacking expression of toll-like receptor 4 (TLR4) by endogenous autogeneic innate immune cells, as well as methods and compositions for engraftment of xenogeneic hematopoietic stem cells in the immunodeficient non-human animal lacking expression of toll-like receptor 4 (TLR4), thereby creating an innate immune system in the animal derived from the xenogeneic hematopoietic stem cells. Further described are immunodeficient mice lacking expression of toll-like receptor 4 by endogenous autogeneic innate immune cells, as well as methods and compositions for engraftment of xenogeneic hematopoietic stem cells in the immunodeficient mouse lacking expression of toll-like receptor 4, thereby creating an innate immune system in the animal derived from the xenogeneic hematopoietic stem cells.

7 Claims, 29 Drawing Sheets

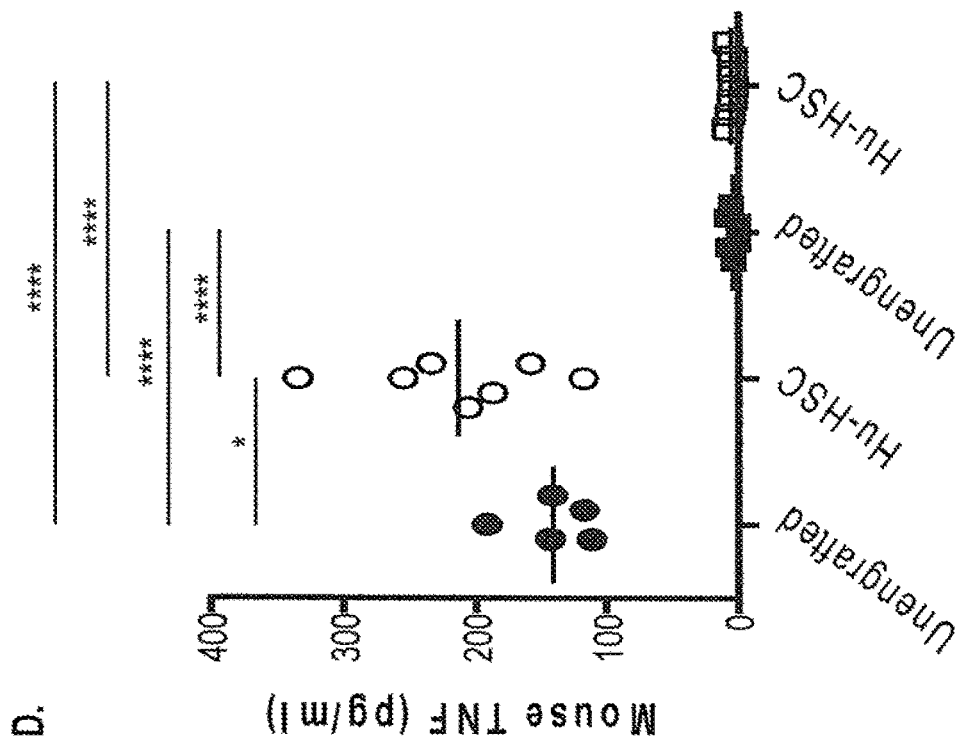
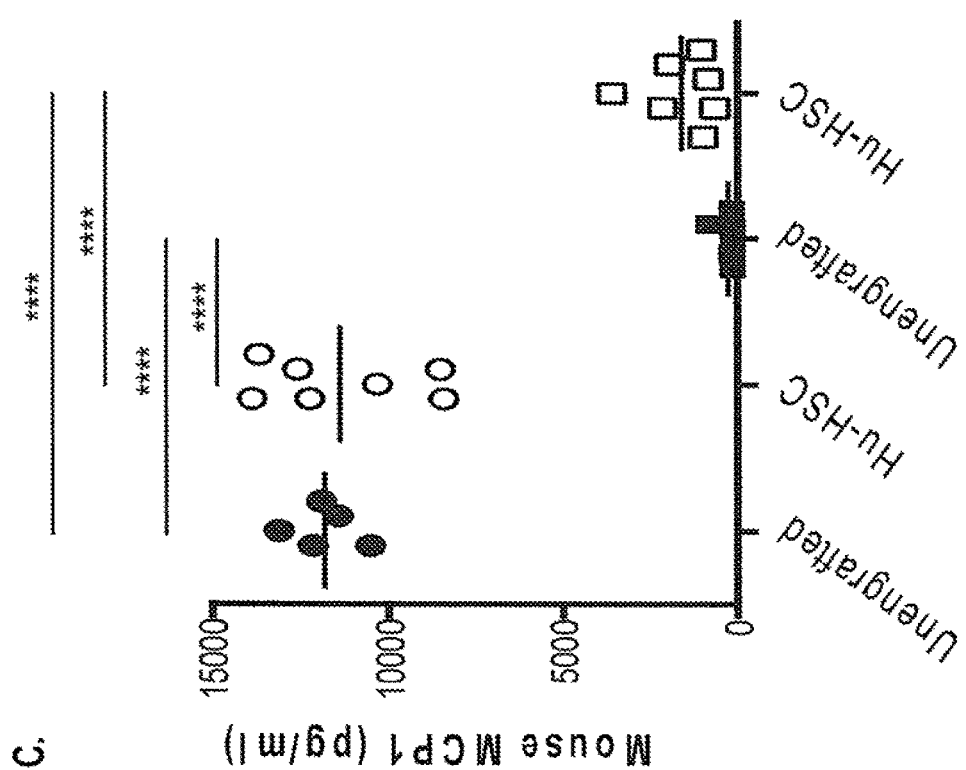
FIG. 8D
FIG. 8C

GENETICALLY MODIFIED NON-HUMAN ANIMALS AND METHODS RELATING TO INNATE IMMUNE SYSTEM RESPONSE DETECTION

REFERENCE TO RELATED APPLICATION

This application is a continuation of U.S. patent application Ser. No. 14/511,793, filed Oct. 10, 2014, which claims priority to U.S. Provisional Patent Application Ser. No. 61/889,804, filed Oct. 11, 2013, the entire content of both of which is incorporated herein by reference.

GOVERNMENT SUPPORT

This invention was made with government support under Grant No. AI046629, awarded by the National Institutes of Health. The Government has certain rights in the invention.

FIELD OF THE INVENTION

The present invention relates generally to immunodeficient non-human animals lacking expression of toll-like receptor 4 (TLR4) by endogenous autogeneic innate immune cells, as well as methods and compositions for engraftment of xenogeneic hematopoietic stem cells in the immunodeficient non-human animal lacking expression of toll-like receptor 4 (TLR4), thereby creating an innate immune system in the animal derived from the xenogeneic hematopoietic stem cells. In specific aspects, the present invention relates to immunodeficient mice lacking expression of toll-like receptor 4 by endogenous autogeneic innate immune cells, as well as methods and compositions for engraftment of xenogeneic hematopoietic stem cells in the immunodeficient mouse lacking expression of toll-like receptor 4, thereby creating an innate immune system in the animal derived from the xenogeneic hematopoietic stem cells.

BACKGROUND OF THE INVENTION

The immune system of vertebrates is extremely complex and disorders of the immune system are likewise complicated. The innate immune system, also called the non-specific immune system, includes cells that defend an organism in a non-specific manner. The innate immune system is distinct from the adaptive immune system which specifically recognizes antigens and provides long-term protection. The innate immune system is characterized antigen-independent response and exposure of the innate immune system does not result in immunologic memory. Cells of the innate immune system include dendritic cells, mast cells, macrophages, natural killer cells, neutrophils, basophils and eosinophils.

Due to the complexity of the vertebrate immune system, diseases and defects are often difficult to characterize and treat. There is a continuing need for animal models which allow for isolation of aspects of the innate immune response, providing methods and compositions useful, for example, for identification of effective medical and pharmaceutical treatments of diseases and defects of the innate immune system.

SUMMARY OF THE INVENTION

Genetically modified immunodeficient non-human animals are provided by the present invention wherein the genome of the genetically modified immunodeficient non-human animals includes a disrupted toll-like receptor 4 gene such that the genetically modified immunodeficient non-human animals lacks the capacity to express the toll-like receptor 4 gene.

Genetically modified immunodeficient non-human animals are provided by the present invention wherein the genome of the genetically modified immunodeficient non-human animals includes a disrupted toll-like receptor 4 gene such that the genetically modified immunodeficient non-human animals lack the capacity to express the toll-like receptor 4 gene, and wherein the animals have severe combined immunodeficiency.

Genetically modified immunodeficient non-human animals are provided by the present invention wherein the genome of the genetically modified immunodeficient non-human animals includes a disrupted toll-like receptor 4 gene such that the genetically modified immunodeficient non-human animals lack the capacity to express the toll-like receptor 4 gene, and wherein the animals has an IL2 receptor gamma chain deficiency.

Genetically modified immunodeficient non-human animals according to aspects of the present invention are rodents.

Genetically modified immunodeficient mice are provided by the present invention wherein the genome of the genetically modified immunodeficient mice includes a disrupted toll-like receptor 4 gene such that the genetically modified immunodeficient mice lack the capacity to express the toll-like receptor 4 gene.

Genetically modified immunodeficient mice are provided by the present invention wherein the genome of the genetically modified immunodeficient mice includes a disrupted toll-like receptor 4 gene such that the genetically modified immunodeficient mice lack the capacity to express the toll-like receptor 4 gene, and wherein the mice have severe combined immunodeficiency.

Genetically modified immunodeficient mice are provided by the present invention wherein the genome of the genetically modified immunodeficient mice includes a disrupted toll-like receptor 4 gene such that the genetically modified immunodeficient mice lacks the capacity to express the toll-like receptor 4 gene, and wherein the animal has an IL2 receptor gamma chain deficiency.

Genetically modified immunodeficient mice are provided by the present invention wherein the genome of the genetically modified immunodeficient mice includes the scid mutation, and wherein the genome of the genetically modified immunodeficient mice includes a disrupted toll-like receptor 4 gene such that the genetically modified immunodeficient mice lack the capacity to express the toll-like receptor 4 gene.

Genetically modified immunodeficient mice are provided by the present invention wherein the genome of the genetically modified immunodeficient mice includes the scid mutation, wherein the animal has an IL2 receptor gamma chain deficiency and wherein the genome of the genetically modified immunodeficient mice includes a disrupted toll-like receptor 4 gene such that the genetically modified immunodeficient mice lack the capacity to express the toll-like receptor 4 gene.

Genetically modified immunodeficient mice are provided by the present invention wherein the genome of the genetically modified immunodeficient mice is homozygous for the scid mutation, and wherein the genome of the genetically modified immunodeficient mice includes a disrupted toll-like receptor 4 gene such that the genetically modified immunodeficient mice lack the capacity to express the toll-like receptor 4 gene.

Genetically modified immunodeficient mice are provided by the present invention wherein the genome of the genetically modified immunodeficient mice is homozygous for the scid mutation, wherein the animal has an IL2 receptor gamma chain deficiency and wherein the genome of the genetically modified immunodeficient mice includes a disrupted toll-like receptor 4 gene such that the genetically modified immunodeficient mice lack the capacity to express the toll-like receptor 4 gene.

Genetically modified immunodeficient non-human animals are provided by the present invention, wherein the genetically modified immunodeficient animal is a NOD.Cg-Prkdcscid Il2rgtm1 Wjl/SzJ mouse having a disrupted toll-like receptor 4 gene such that the mouse lacks the capacity to express the toll-like receptor 4 gene.

A NOD.Cg-Prkdc$^{scid}$Il2rg$^{tm1Wjl}$Tlr4$^{Lps-Del}$/SzJ (NSG-TLR4$^{null}$) mouse is provided by the present invention.

Isolated cells of genetically modified immunodeficient non-human animals are provided by the present invention, wherein mice have a disrupted toll-like receptor 4 gene such that the mice lack the capacity to express the toll-like receptor 4 gene.

Isolated cells of genetically modified immunodeficient non-human animals are provided by the present invention, wherein the genetically modified immunodeficient animal is a NOD.Cg-Prkdcscid Il2rgtm1 Wjl/SzJ mouse having a disrupted toll-like receptor 4 gene such that the mouse lacks the capacity to express the toll-like receptor 4 gene.

According to aspects of the present invention, genetically modified immunodeficient non-human animals of the present invention further include xenogeneic haematopoietic stem cells. According to aspects of the present invention, genetically modified immunodeficient non-human animals of the present invention further include human haematopoietic stem cells.

According to aspects of the present invention, genetically modified immunodeficient non-human animals of the present invention further include xenogeneic innate immune cells.

According to aspects of the present invention, genetically modified immunodeficient non-human animals of the present invention further include human innate immune cells.

According to aspects of the present invention, genetically modified immunodeficient mice of the present invention further include xenogeneic haematopoietic stem cells. According to aspects of the present invention, genetically modified immunodeficient mice of the present invention further include human haematopoietic stem cells.

According to aspects of the present invention, genetically modified immunodeficient mice of the present invention further include xenogeneic innate immune cells.

According to aspects of the present invention, genetically modified immunodeficient mice further of the present invention include human innate immune cells.

A NOD.Cg-Prkdc$^{scid}$Il2rg$^{tm1Wjl}$Tlr4$^{Lps-Del}$/SzJ (NSG-TLR4$^{null}$) mouse is provided by the present invention.

A NOD.Cg-Prkdc$^{scid}$Il2rg$^{tm1Wjl}$Tlr4$^{Lps-Del}$/SzJ (NSG-TLR4$^{null}$) mouse including xenogeneic CD34+ cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including human CD34+ cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including xenogeneic HSC cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including human HSC cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including human innate immune cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including xenogeneic innate immune cells is provided by the present invention.

A NOD.Cg-Prkdc$^{scid}$Il2rg$^{tm1Wjl}$Tlr4$^{Lps-Del}$/SzJ (NSG-TLR4$^{null}$) mouse including human innate immune cells is provided by the present invention.

Methods for producing a non-human animal model system for response of xenogeneic innate immune cells, are provided according to aspects of the present invention which include providing a non-human genetically modified immunodeficient animal comprising a disrupted toll-like receptor 4 gene such that the non-human genetically modified immunodeficient animal lacks the capacity to express the toll-like receptor 4 gene; and administering xenogeneic haematopoietic stem cells to the non-human genetically modified immunodeficient animal.

Methods for producing a non-human animal model system for response of xenogeneic innate immune cells, are provided according to aspects of the present invention which include providing a non-human genetically modified immunodeficient animal comprising a disrupted toll-like receptor 4 gene such that the non-human genetically modified immunodeficient animal lacks the capacity to express the toll-like receptor 4 gene, wherein the non-human genetically modified immunodeficient animal has severe combined immunodeficiency; and administering xenogeneic haematopoietic stem cells to the non-human genetically modified immunodeficient animal.

Methods for producing a non-human animal model system for response of xenogeneic innate immune cells, are provided according to aspects of the present invention which include providing a non-human genetically modified immunodeficient animal comprising a disrupted toll-like receptor 4 gene such that the non-human genetically modified immunodeficient animal lacks the capacity to express the toll-like receptor 4 gene, wherein the non-human genetically modified immunodeficient animal has severe combined immunodeficiency and wherein the non-human genetically modified immunodeficient has an IL2 receptor gamma chain deficiency; and administering xenogeneic haematopoietic stem cells to the non-human genetically modified immunodeficient animal.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genetically modified immunodeficient mouse has severe combined immunodeficiency; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genetically modified immunodeficient mouse has severe combined immunodeficiency and wherein the genetically modified immunodeficient has an IL2 receptor gamma chain deficiency; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice includes the scid mutation; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice includes the scid mutation and wherein the genetically modified immunodeficient mouse has severe combined immunodeficiency; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice includes the scid mutation, wherein the genetically modified immunodeficient mouse has severe combined immunodeficiency and wherein the genetically modified immunodeficient mouse has an IL2 receptor gamma chain deficiency; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice is homozygous for the scid mutation; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice is homozygous for the scid mutation and wherein the genetically modified immunodeficient mouse has severe combined immunodeficiency; and administering xenogeneic haematopoietic stem cells to the genetically modified immunodeficient mouse.

Methods for producing a mouse model system for response of xenogeneic innate immune cells, are provided according to aspects of the present invention which include providing a genetically modified immunodeficient mouse comprising a disrupted toll-like receptor 4 gene such that the genetically modified immunodeficient mouse lacks the capacity to express the toll-like receptor 4 gene, wherein the genome of the genetically modified immunodeficient mice is homozygous for the scid mutation, wherein the genetically modified immunodeficient mouse has severe combined immunodeficiency and wherein the genetically modified immunodeficient mouse has an IL2 receptor gamma chain deficiency; and administering xenogeneic haematopoietic stem cells to the genetically modified immunodeficient mouse.

Methods for producing a mouse model system for response of xenogeneic innate immune cells, are provided according to aspects of the present invention which include providing a NOD.Cg-Prkdcscid Il2rgtm1Wjl/SzJ mouse comprising a disrupted toll-like receptor 4 gene such that the mouse lacks the capacity to express the toll-like receptor 4 gene; and administering xenogeneic haematopoietic stem cells to the NOD.Cg-Prkdcscid Il2rgtm1Wjl/SzJ mouse having a disrupted toll-like receptor 4 gene such that the mouse lacks the capacity to express the toll-like receptor 4 gene.

According to aspects of the present invention, the xenogeneic haematopoietic stem cells administered to the genetically modified immunodeficient mouse comprising a disrupted toll-like receptor 4 gene such that the genetically modified immunodeficient mouse lacks the capacity to express the toll-like receptor 4 gene are human haematopoietic stem cells.

According to aspects of the present invention, the xenogeneic haematopoietic stem cells administered to a NOD.Cg-Prkdcscid Il2rgtm1 Wjl/SzJ mouse having a disrupted toll-like receptor 4 gene such that the mouse lacks the capacity to express the toll-like receptor 4 gene are human haematopoietic stem cells.

According to aspects of the present invention, xenogeneic haematopoietic stem cells are administered to a NOD.Cg-Prkdc$^{scid}$Il2rg$^{tm1\,Wjl}$Tlr4$^{Lps\text{-}Del}$/SzJ (NSG-TLR4$^{null}$) mouse.

According to aspects of the present invention, human haematopoietic stem cells are administered to a NOD.Cg-Prkdc$^{scid}$Il2rg$^{tm1\,Wjl}$Tlr4$^{Lps\text{-}Del}$/SzJ (NSG-TLR4$^{null}$) mouse.

Methods for identifying modulators of an innate immune system response are provided according to the present invention which include providing a non-human genetically modified immunodeficient animal comprising a disrupted toll-like receptor 4 gene such that the non-human genetically modified immunodeficient animal lacks the capacity to express the toll-like receptor 4 gene; administering xenogeneic haematopoietic stem cells to the non-human genetically modified immunodeficient animal, wherein the xenogeneic haematopoietic stem cells differentiate to produce xenogeneic innate immune cells in the non-human genetically modified immunodeficient animal; administering an innate immune system stimulator to the animal; administering a test compound to the animal; assaying a response of the xenogeneic innate immune cells to the stimulator; and comparing the response to a standard to determine the effect of the test compound on the response of the xenogeneic innate immune cells to the stimulator, wherein an effect of the test compound identifies a modulator of the xenogeneic innate immune system in the animal.

Methods for identifying modulators of an innate immune system response are provided according to the present invention which include providing a non-human genetically modified immunodeficient animal comprising a disrupted toll-like receptor 4 gene such that the non-human genetically modified immunodeficient animal lacks the capacity to express the toll-like receptor 4 gene; administering xenogeneic haematopoietic stem cells to the non-human genetically modified immunodeficient animal, wherein the xenogeneic haematopoietic stem cells differentiate to produce xenogeneic innate immune cells in the non-human genetically modified immunodeficient animal; administering Gram negative bacterial lipopolysaccharides (LPS), Lipid A and/or morphine-3-glucuronide as an innate immune system stimulator to the animal; administering a test compound to the animal; assaying a response of the xenogeneic innate immune cells to the stimulator; and comparing the response to a standard to determine the effect of the test compound on the response of the xenogeneic innate immune cells to the stimulator, wherein an effect of the test compound identifies a modulator of the xenogeneic innate immune system in the animal.

Optionally, one or more of CD80, CD86, IL6, IL8, IL10 and IL1β is assayed in the animal to determine the effect of the test compound on the innate immune response of the animal to the innate immune system stimulator.

According to aspects of methods for identifying modulators of an innate immune system response, the non-human genetically modified immunodeficient animal is a mouse and the xenogeneic haematopoietic stem cells are human haematopoietic stem cells.

According to aspects of methods for identifying modulators of an innate immune system response, the non-human genetically modified immunodeficient animal is a NOD.Cg-Prkdcscid Il2rgtm1 Wjl/SzJ mouse having a disrupted toll-like receptor 4 gene such that the mouse lacks the capacity to express the toll-like receptor 4 gene and the xenogeneic haematopoietic stem cells are human haematopoietic stem cells.

According to aspects of methods for identifying modulators of an innate immune system response, the non-human genetically modified immunodeficient animal is a NOD.Cg-Prkdc$^{scid}$Il2rg$^{tm1\ Wjl}$Tlr4$^{Lps-Del}$/SzJ (NSG-TLR4$^{null}$) mouse and the xenogeneic haematopoietic stem cells are human haematopoietic stem cells.

According to aspects of methods for identifying modulators of an innate immune system response, the non-human genetically modified immunodeficient animal is a genetically modified immunodeficient rodent having a disrupted toll-like receptor 4 gene such that the mouse lacks the capacity to express the toll-like receptor 4 gene and the xenogeneic haematopoietic stem cells are human haematopoietic stem cells.

BRIEF DESCRIPTION OF THE DRAWINGS

FIG. 8C is a graph showing results of an assay for murine MCP1 in serum samples from HSC-engrafted NSG and NSG-TLR4$^{null}$ mice at 6 hours after LPS or PBS treatment;

FIG. 8D is a graph showing results of an assay for murine TNF in serum samples from HSC-engrafted NSG and NSG-TLR4$^{null}$ mice at 6 hours after LPS or PBS treatment;

Figure 1A:
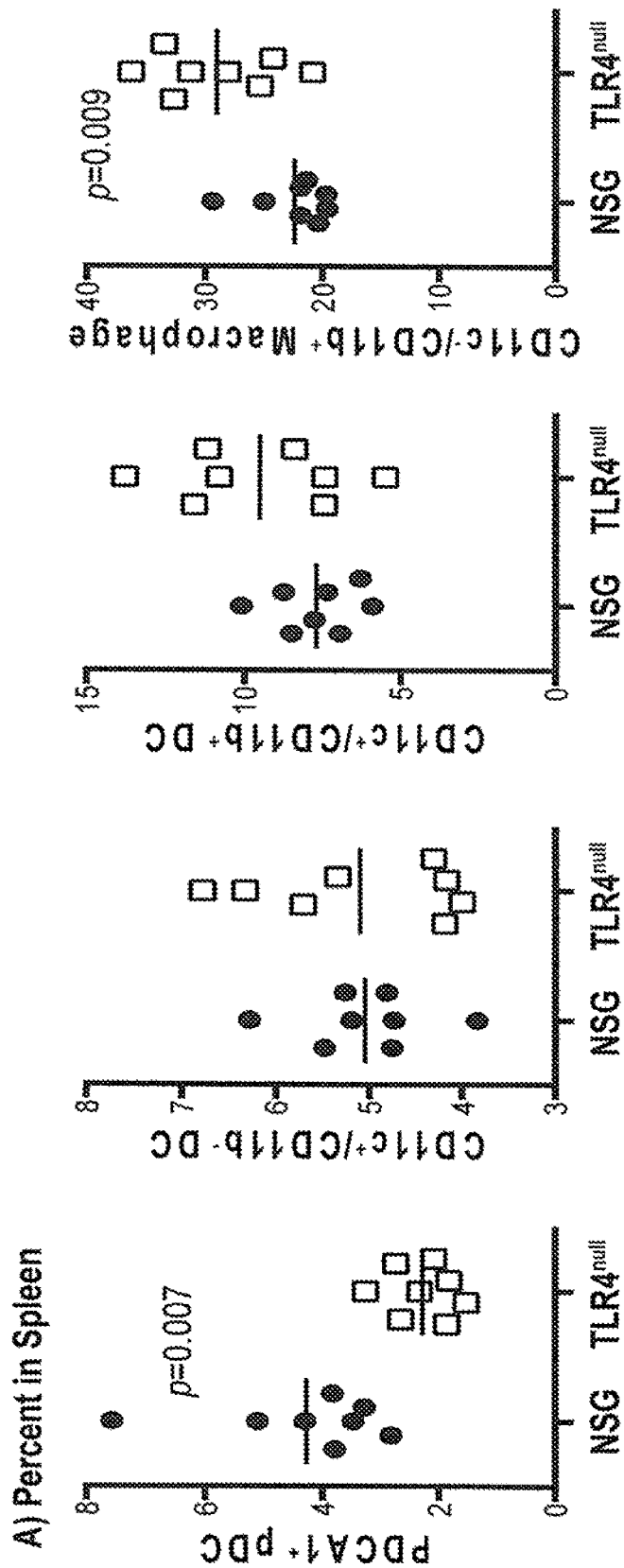
FIG. 1A shows graphs indicating the percentages of mouse innate immune cells, mouse PDCA1+(CD317) plasmacytoid dendritic cells, CD11c+/CD11b− dendritic cells, CD11c+CD11b+ dendritic cells, and CD11c−/CD11b+ macrophages in spleen were comparable for NSG and NSG-TLR4$^{null}$ mice.
Figure 1B:
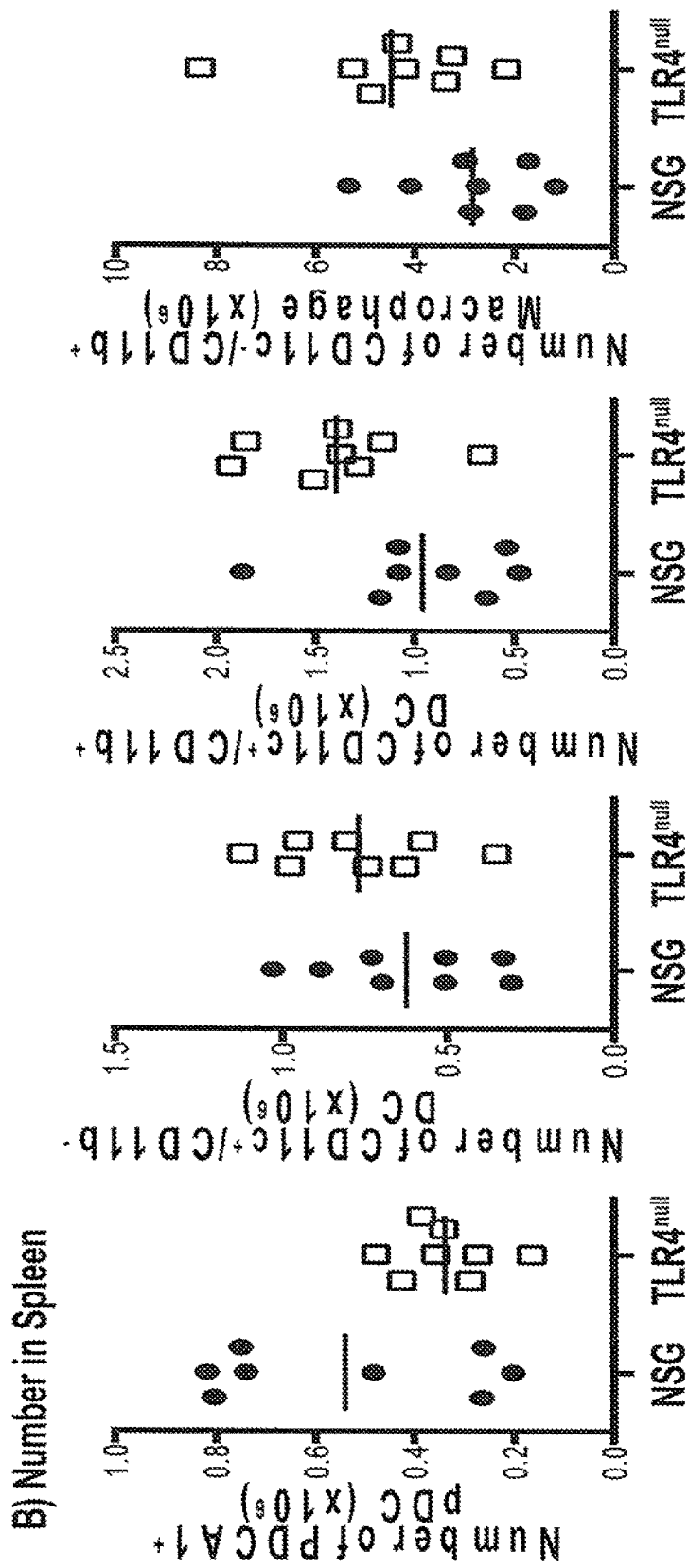
FIG. 1B shows graphs indicating the total number of mouse innate immune cells, mouse PDCA1+(CD317) plasmacytoid dendritic cells, CD11c+/CD11b− dendritic cells, CD11c+CD11b+ dendritic cells, and CD11c−/CD11b+ macrophages in spleen were comparable for NSG and NSG-TLR4$^{null}$ mice.
Figure 1C:
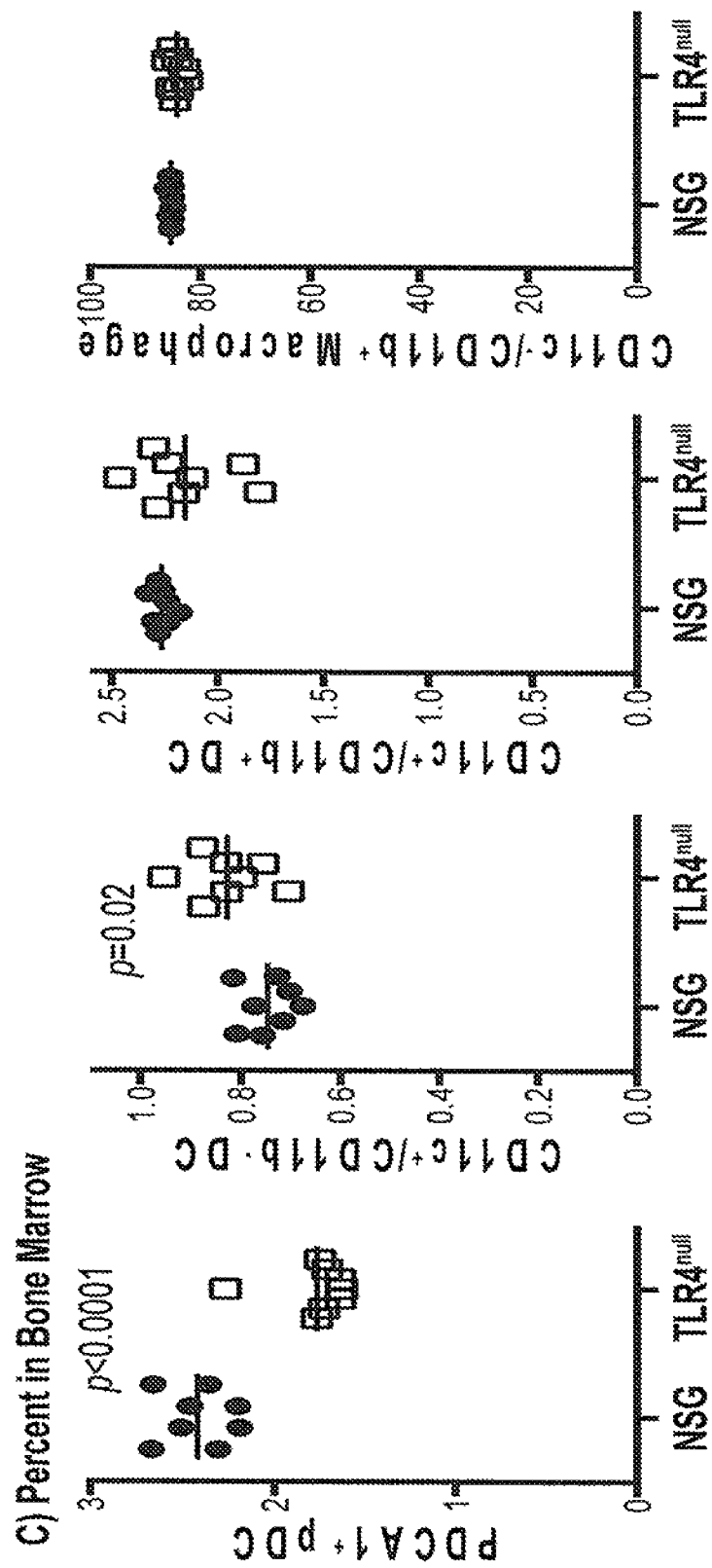
FIG. 1C shows graphs indicating the percentages of mouse innate immune cells, mouse PDCA1+(CD317) plasmacytoid dendritic cells, CD11c+/CD11b− dendritic cells, CD11c+CD11b+ dendritic cells, and CD11c−/CD11b+ macrophages in bone marrow were comparable for NSG and NSG-TLR4$^{null}$ mice.
Figure 1D:
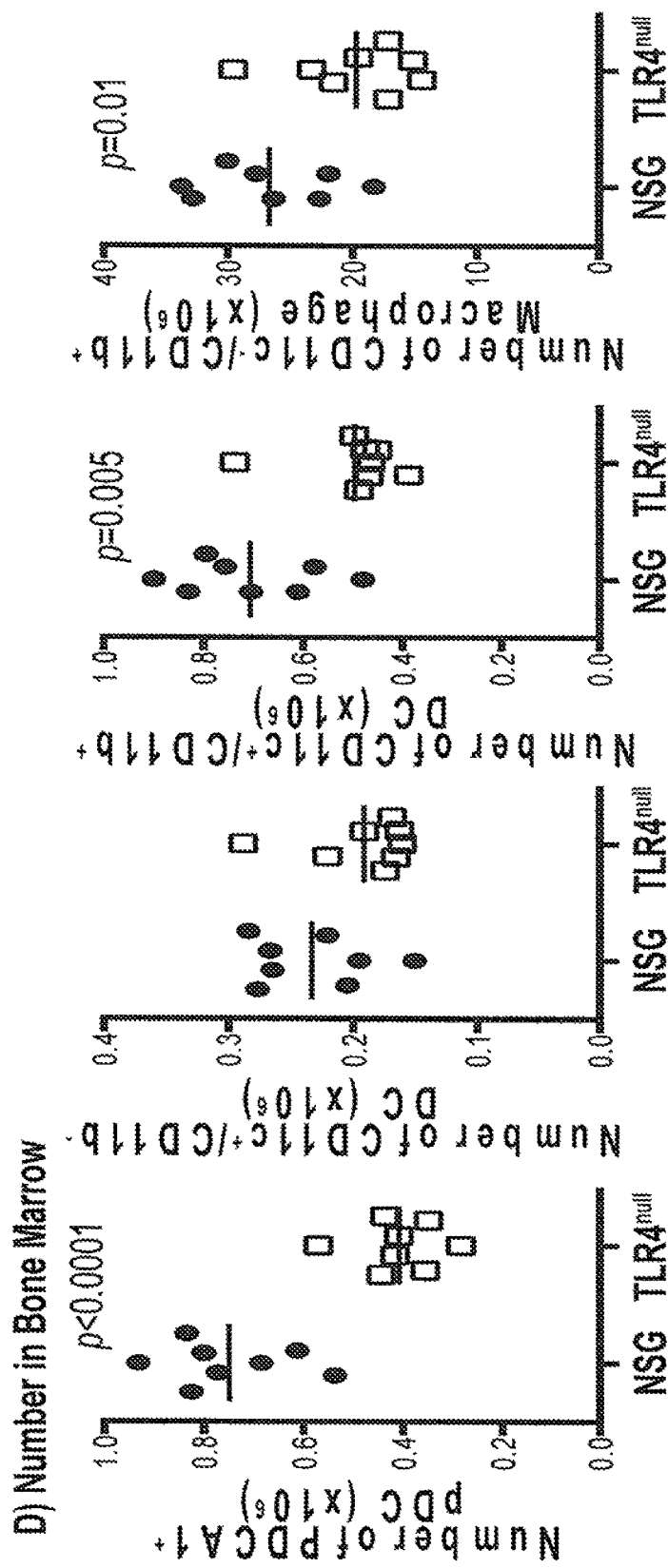
FIG. 1D shows graphs indicating the total number of mouse innate immune cells, mouse PDCA1+(CD317) plasmacytoid dendritic cells, CD11c+/CD11b− dendritic cells, CD11c+CD11b+ dendritic cells, and CD11c−/CD11b+ macrophages in bone marrow were comparable for NSG and NSG-TLR4$^{null}$ mice.
Figure 2B:
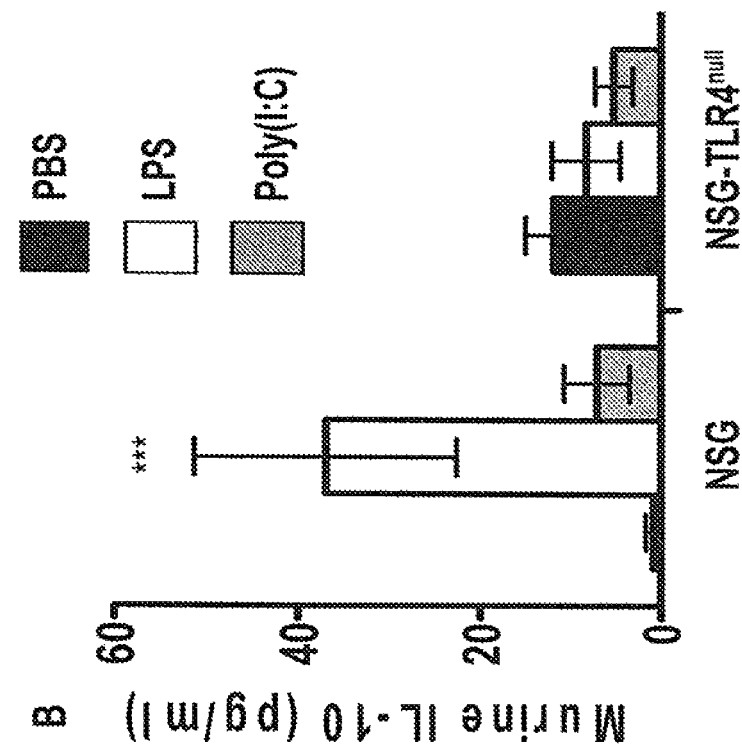
FIG. 2B is a graph showing results of an assay for murine IL-10 in serum samples from NSG and NSG-TLR4$^{null}$ mice injected IP with 100 μg of either LPS or poly(I:C) compared to mice injected IP with phosphate buffered saline (PBS)
Figure 2A:
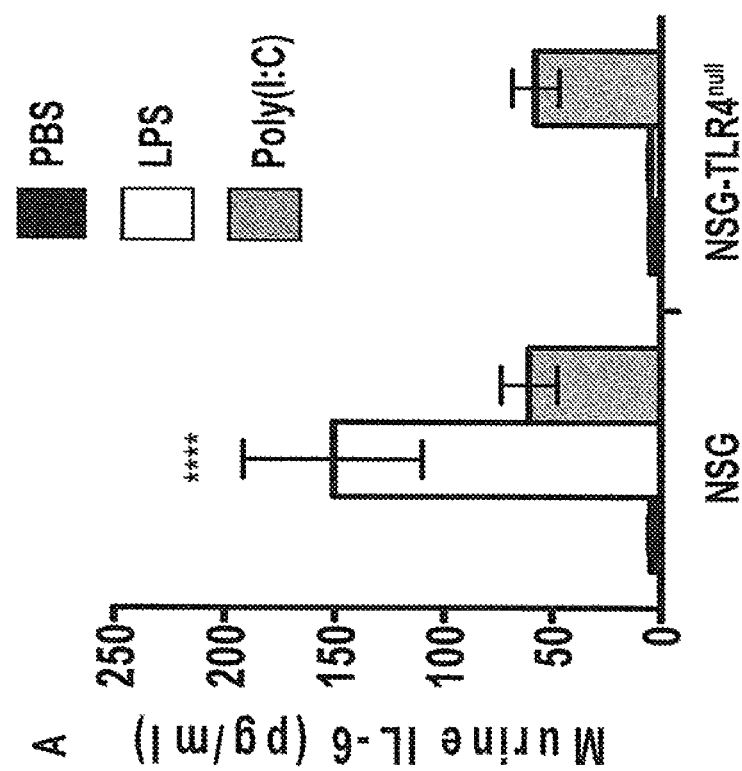
FIG. 2A is a graph showing results of an assay for murine IL-6 in serum samples from NSG and NSG-TLR4$^{null}$ mice injected IP with 100 μg of either LPS or poly(I:C) compared to mice injected IP with phosphate buffered saline (PBS)
Figure 2C:
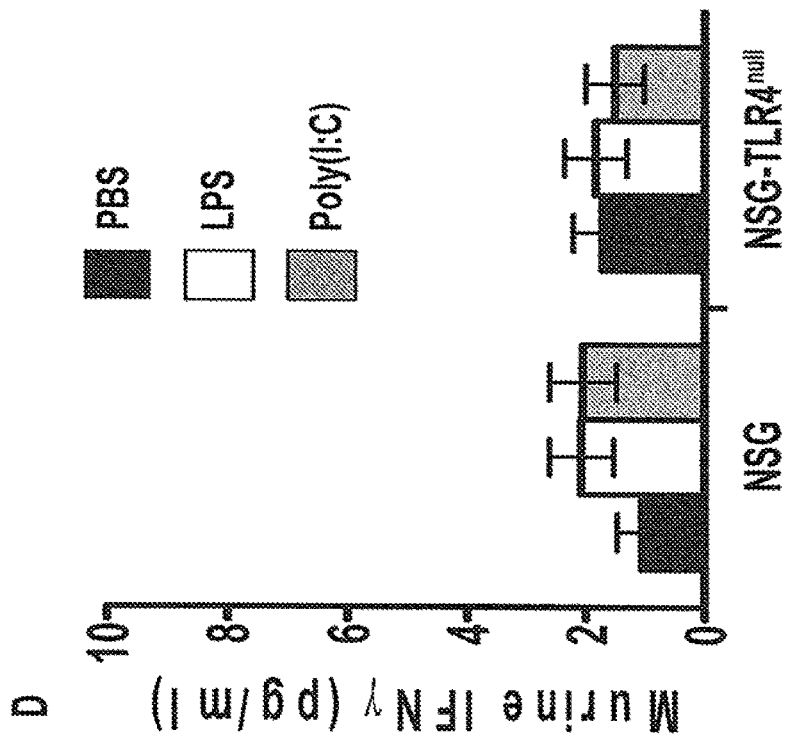
FIG. 2C is a graph showing results of an assay for murine MCP1 in serum samples from NSG and NSG-TLR4$^{null}$ mice injected IP with 100 μg of either LPS or poly(I:C) compared to mice injected IP with phosphate buffered saline (PBS)
Figure 2D:
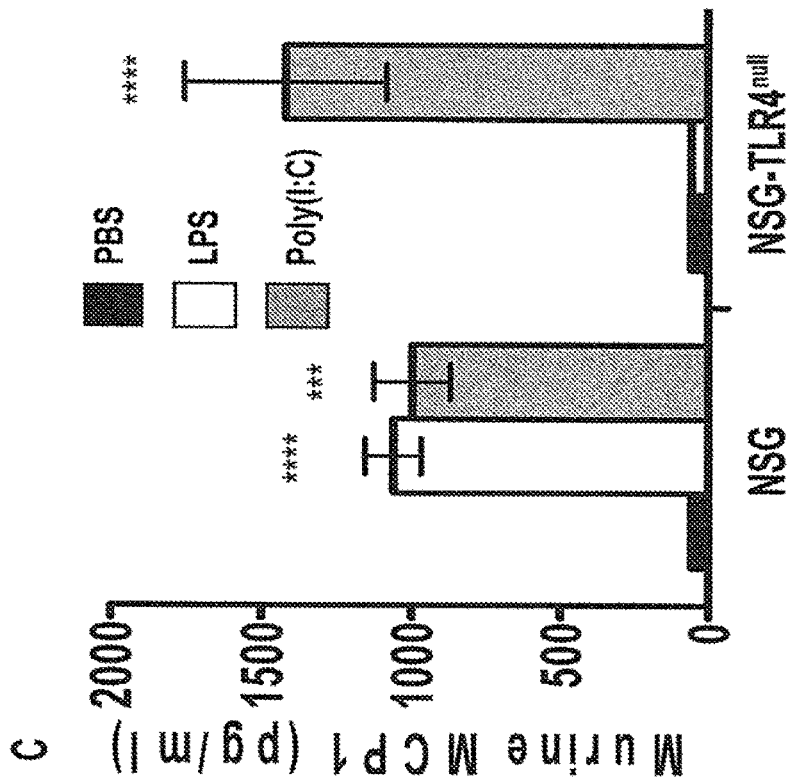
FIG. 2D is a graph showing results of an assay for murine IFNγ in serum samples from NSG and NSG-TLR4$^{null}$ mice injected IP with 100 μg of either LPS or poly(I:C) compared to mice injected IP with phosphate buffered saline (PBS)
Figure 2F:
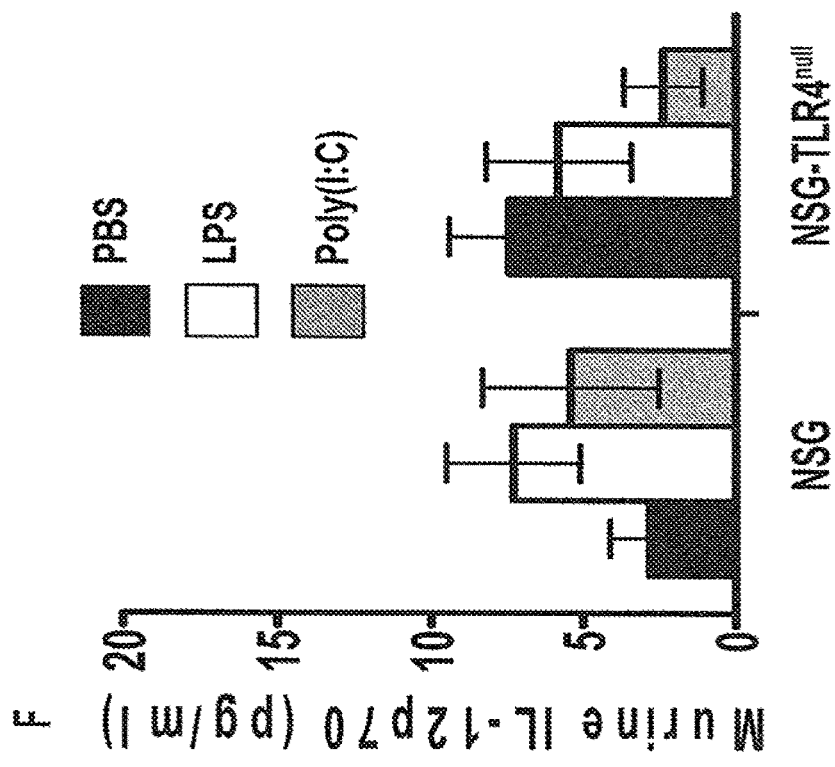
FIG. 2F is a graph showing results of an assay for murine IL-12p70 in serum samples from NSG and NSG-TLR4$^{null}$ mice injected IP with 100 μg of either LPS or poly(I:C) compared to mice injected IP with phosphate buffered saline (PBS)
Figure 2E:
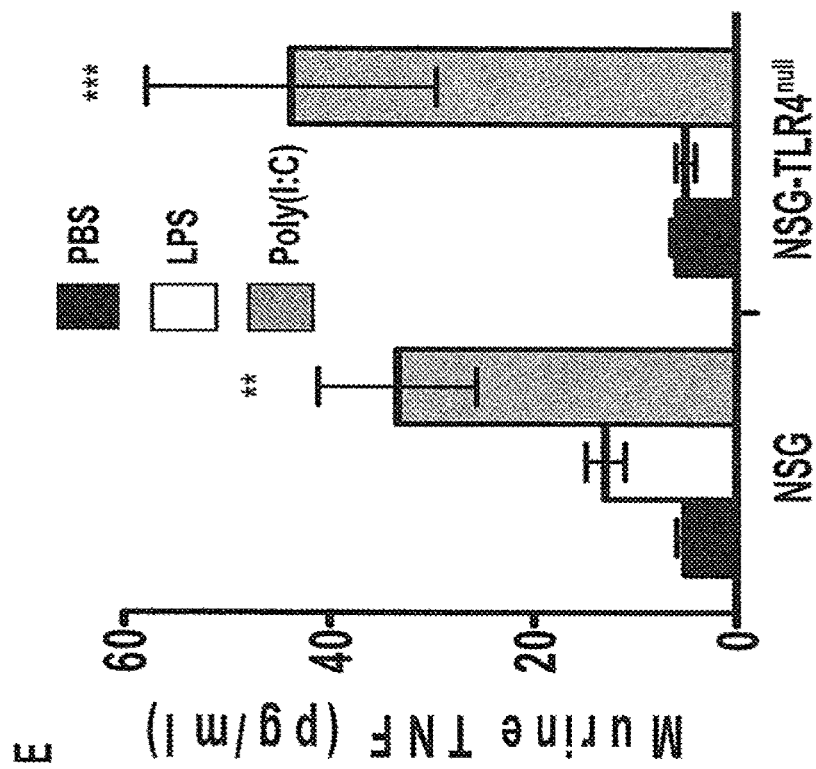
FIG. 2E is a graph showing results of an assay for murine TNF in serum samples from NSG and NSG-TLR4$^{null}$ mice injected IP with 100 μg of either LPS or poly(I:C) compared to mice injected IP with phosphate buffered saline (PBS)
Figures 3A, 3B, 3C:
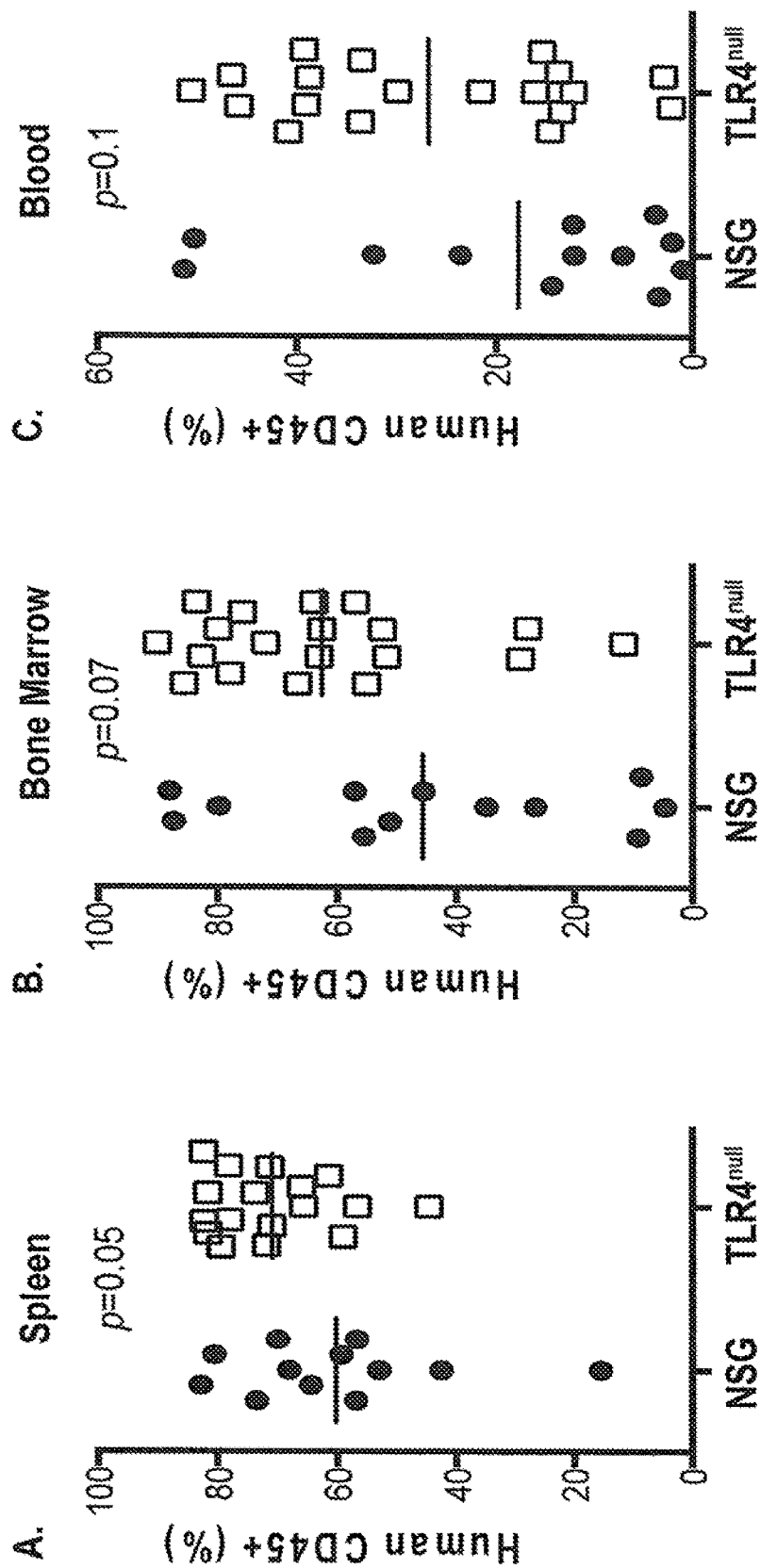
FIG. 3A is a graph showing the percentage of human CD45+ cells in the spleen of newborn conditioned NSG or NSG-TLR4$^{null}$ mice where both types of mice were engrafted with human HSC 16 weeks prior to analysis.
FIG. 3B is a graph showing the percentage of human CD45+ cells in the bone marrow of newborn conditioned NSG or NSG-TLR4$^{null}$ mice where both types of mice were engrafted with human HSC 16 weeks prior to analysis.
FIG. 3C is a graph showing the percentage of human CD45+ cells in the blood of newborn conditioned NSG or NSG-TLR4$^{null}$ mice where both types of mice were engrafted with human HSC 16 weeks prior to analysis.
Figures 3D, 3E:
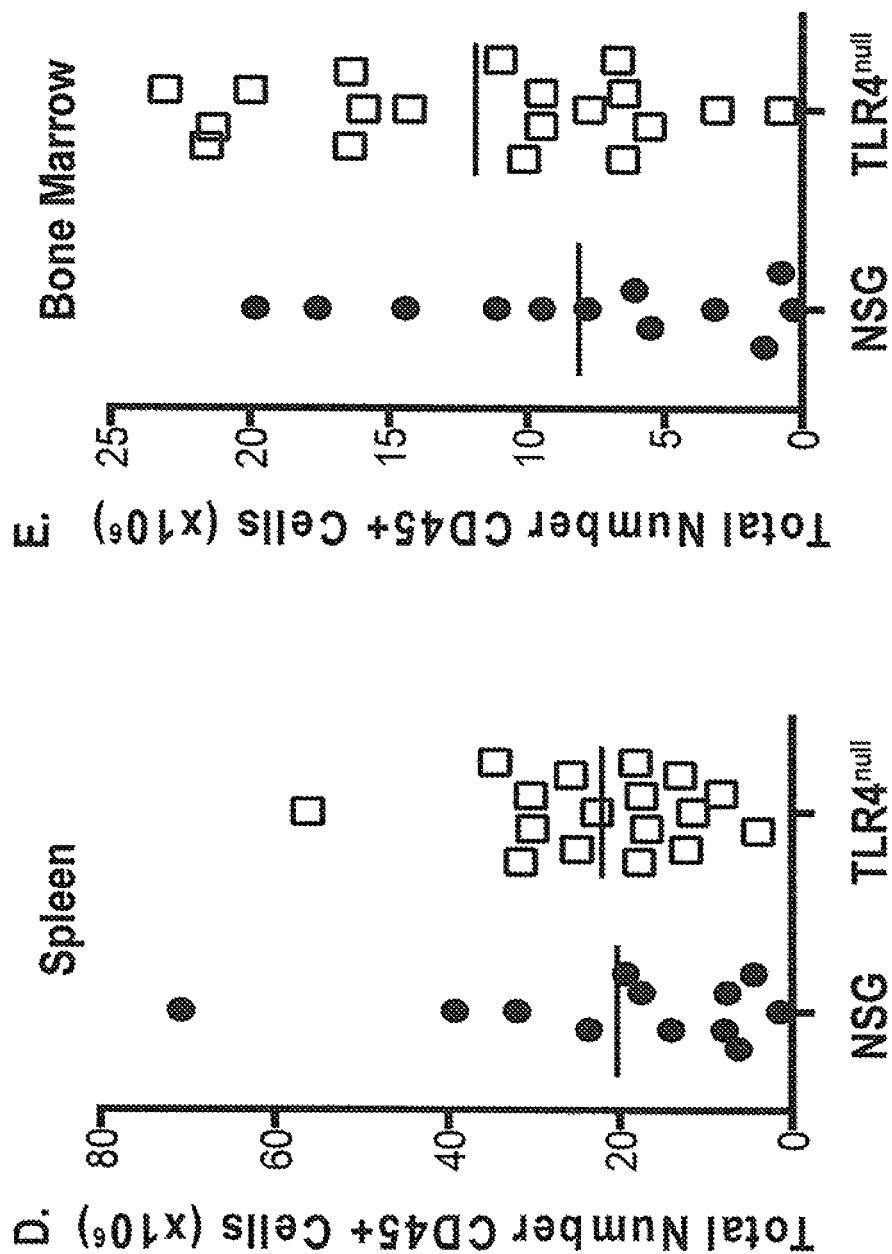
FIG. 3D is a graph showing the total number of human CD45+ cells in the spleen of newborn conditioned NSG or NSG-TLR4$^{null}$ mice where both types of mice were engrafted with human HSC 16 weeks prior to analysis.
FIG. 3E is a graph showing the total number of human CD45+ cells in the bone marrow of newborn conditioned NSG or NSG-TLR4$^{null}$ mice where both types of mice were engrafted with human HSC 16 weeks prior to analysis.
Figures 4A, 4B, 4C:
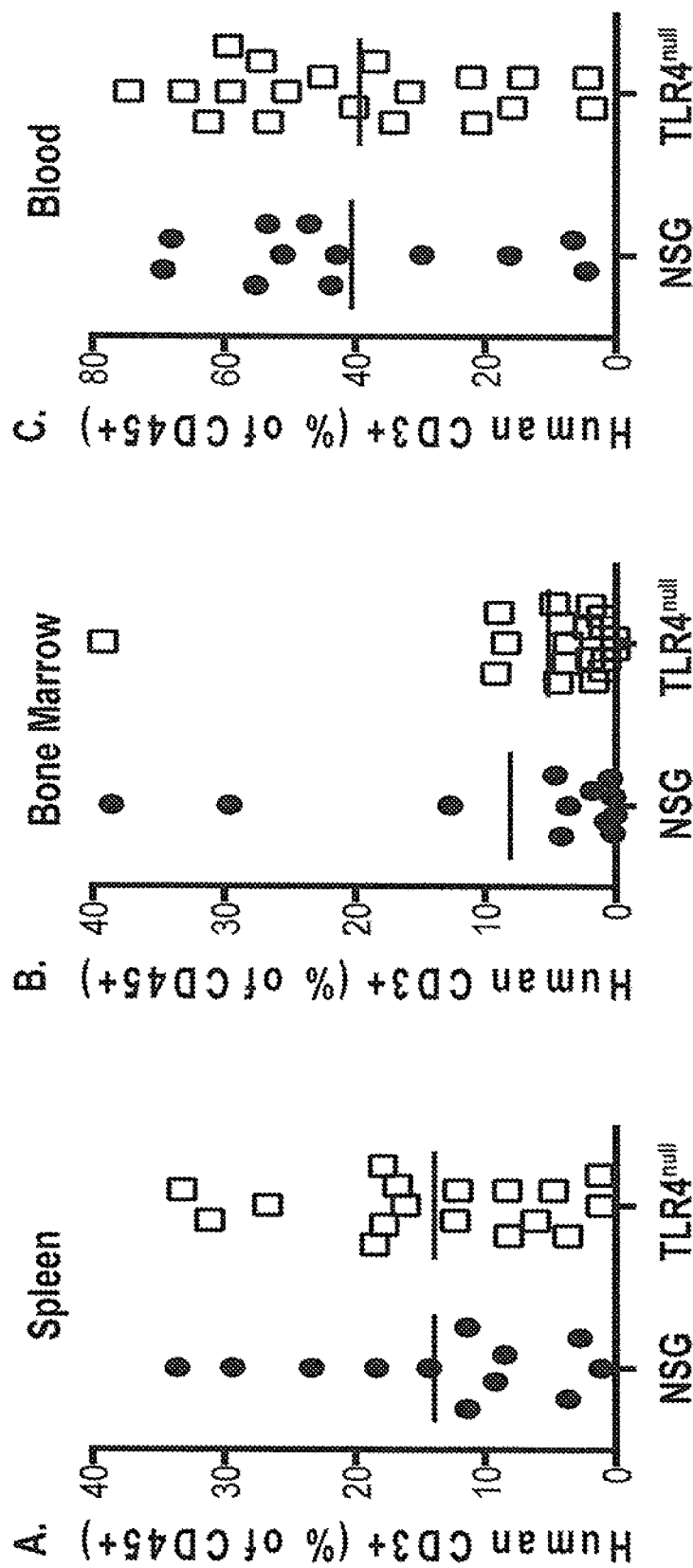
FIG. 4A is a graph showing the percentage of human CD3+ cells in the spleen of NSG or NSG-TLR4$^{null}$ mice engrafted with human HSC 16 weeks prior to analysis.
FIG. 4B is a graph showing the percentage of human CD3+ cells in the bone marrow of NSG or NSG-TLR4$^{null}$ mice engrafted with human HSC 16 weeks prior to analysis.
FIG. 4C is a graph showing the percentage of human CD3+ cells in the blood of NSG or NSG-TLR4$^{null}$ mice engrafted with human HSC 16 weeks prior to analysis.
Figures 4D, 4E, 4F:
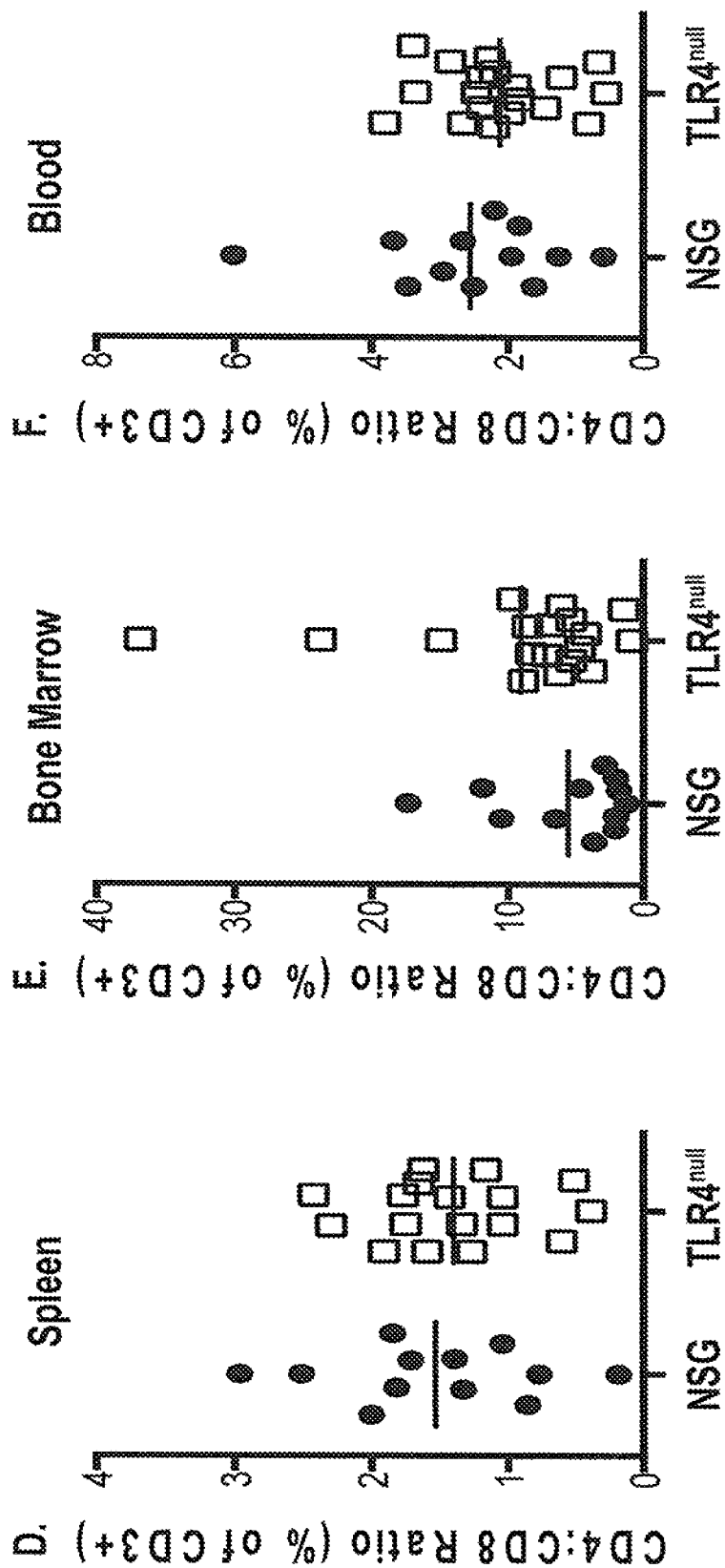
FIG. 4D is a graph showing the CD4:CD8 T cell ratio in the spleen of NSG or NSG-TLR4$^{null}$ mice engrafted with human HSC 16 weeks prior to analysis.
FIG. 4E is a graph showing the CD4:CD8 T cell ratio in the bone marrow of NSG or NSG-TLR4$^{null}$ mice engrafted with human HSC 16 weeks prior to analysis.
FIG. 4F is a graph showing the CD4:CD8 T cell ratio in the blood of NSG or NSG-TLR4$^{null}$ mice engrafted with human HSC 16 weeks prior to analysis.
Figures 4G, 4H, 4I:
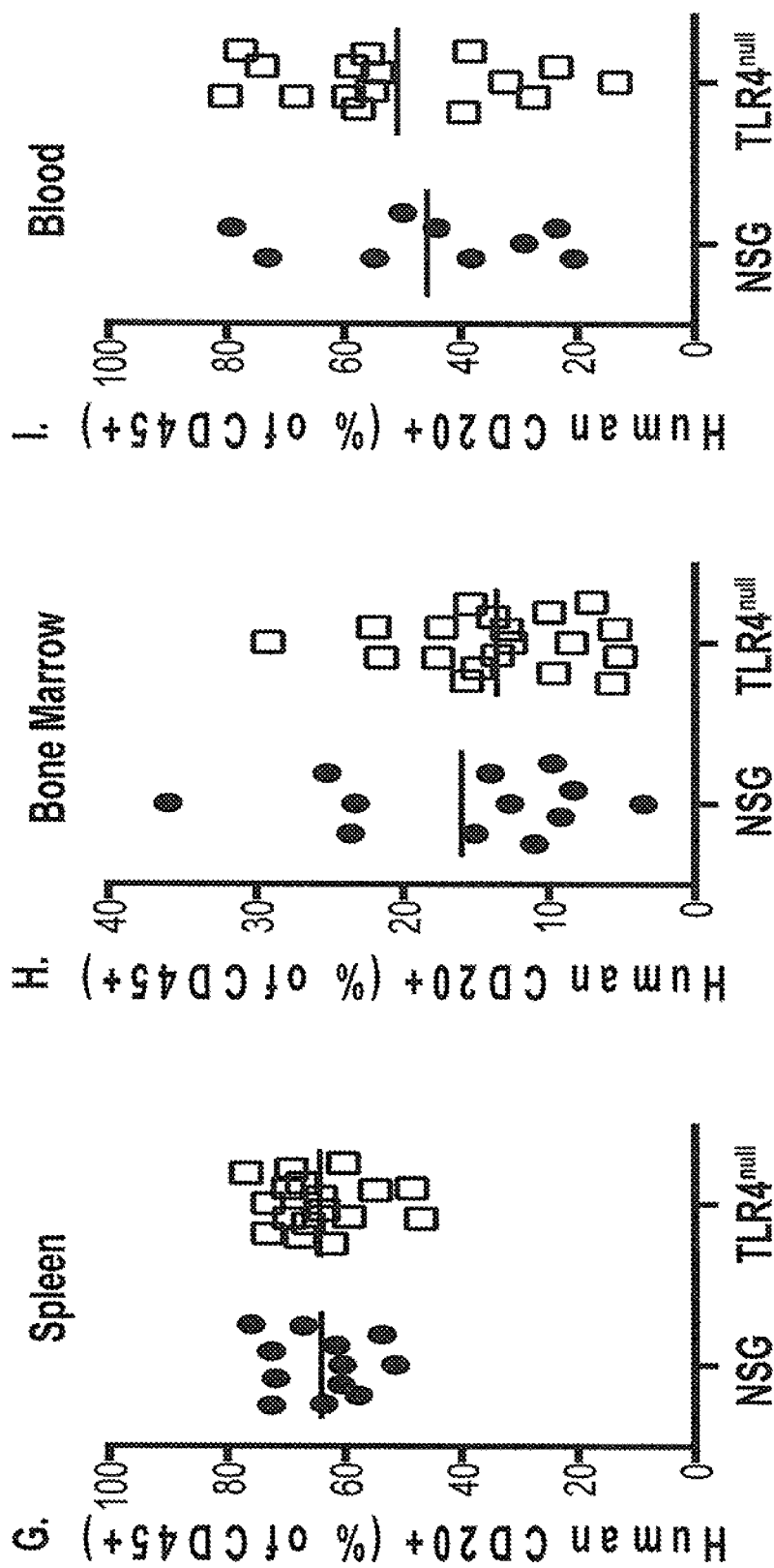
FIG. 4G is a graph showing the percentage of human CD20+ in the spleen of NSG or NSG-TLR4$^{null}$ mice engrafted with human HSC 16 weeks prior to analysis.
FIG. 4H is a graph showing the percentage of human CD20+ cells in the bone marrow of NSG or NSG-TLR4$^{null}$ mice engrafted with human HSC 16 weeks prior to analysis.
FIG. 4I is a graph showing the percentage of human CD20+ cells in the blood of NSG or NSG-TLR4$^{null}$ mice engrafted with human HSC 16 weeks prior to analysis.

The term "severe combined immune deficiency (SCID)" refers to a condition characterized by absence of T cells and lack of B cell function.

Common forms of SCID include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+).

A genetically modified mouse according to aspects of the present invention has the severe combined immunodeficiency mutation (Prkdc$^{scid}$), commonly referred to as the scid mutation. The scid mutation is well-known and located on mouse chromosome 16 as described in Bosma, et al., Immunogenetics 29:54-56, 1989. Mice homozygous for the scid mutation are characterized by an absence of functional T cells and B cells, lymphopenia, hypoglobulinemia and a normal hematopoetic microenvironment. The scid mutation can be detected, for example, by detection of markers for the scid mutation using well-known methods, such as PCR or flow cyotometry.

A genetically modified mouse according to aspects of the present invention has an IL2 receptor gamma chain deficiency. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

Genetically modified immunodeficient mice having the scid mutation or an IL2 receptor gamma chain deficiency in combination with the scid mutation are provided according to aspects of the present invention whose genome includes a disrupted toll-like receptor 4 gene such that the mice are incapable of expressing toll-like receptor 4 or are incapable of expressing toll-like receptor 4 characterized by toll-like receptor 4 activity.

Genetically modified NOD scid gamma mice are provided according to aspects of the present invention whose genome includes a disrupted toll-like receptor 4 gene (Tlr4) such that the mice are incapable of expressing toll-like receptor 4 or are incapable of expressing toll-like receptor 4 characterized by toll-like receptor 4 activity.

The terms "NOD scid gamma" and "NSG" are used interchangeably herein to refer to a well-known immunodeficient mouse strain NOD.Cg-Prkdc$^{scid}$Il2rg$^{tm1Wjl}$/SzJ. NSG mice combine multiple immune deficits from the NOD/ShiLtJ background, the severe combined immune deficiency (scid) mutation, and a complete knockout of the interleukin-2 receptor gamma chain. As a result, NSG mice lack mature T, B and NK cells, and are deficient in cytokine signaling. NSG mice are characterized by lack of IL2R-γ (gamma c) expression, no detectable serum immunoglobulin, no hemolytic complement, no mature T lymphocytes, and no mature natural killer cells.

Genetically modified immunodeficient non-human animals having severe combined immunodeficiency or an IL2 receptor gamma chain deficiency in combination with severe combined immunodeficiency are provided according to aspects of the present invention whose genome includes a disrupted of the toll-like receptor 4 gene.

Toll-like receptor 4 is well-known as a protein having a fundamental role in innate immunity. Toll-like receptor 4 is well-known and well-characterized structurally and functionally in numerous organisms, and is highly conserved among species, sharing structural and functional properties, Rock F L et al, 1998, PNAS 95 (2):588-93; Medzhitov R et al, 1997, Nature 388 (6640):394-7; Re F et al, 2002, J. Biol. Chem. 277 (26):23427-32; and Rhee S H et al, 2000, J. Biol. Chem. 275(44):34035-40.

"Disruption" of the toll-like receptor 4 gene refers to genetic modification of the gene such that expression of toll-like receptor 4 is absent or reduced to 25% or less, 20% or less, 15% or less, 10% or less, or 5% or less, compared to wild-type.

Any of various methods can be used to disrupt the toll-like receptor 4 gene to produce a genetically modified immunodeficient non-human animal whose genome includes a disruption of the toll-like receptor 4 gene. The toll-like receptor 4 gene is disrupted in the genome of genetically modified animals according to standard methods of genetic engineering such as, but not limited to, chemical mutagenesis, irradiation, homologous recombination and transgenic expression of antisense RNA. Such techniques are well-known in the art and further include, but are not limited to, pronuclear microinjection and transformation of embryonic stem cells. Methods for generating genetically modified animals whose genome includes a disrupted gene that can be used include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026.

Generation of a genetically modified immunodeficient non-human animal whose genome includes a disrupted of the toll-like receptor 4 gene can be achieved by introduction of a gene targeting vector into a preimplantation embryo or stem cells, such as embryonic stem (ES) cells or induced pluripotent stem (iPS) cells.

The term "gene targeting vector" refers to a double-stranded recombinant DNA molecule effective to recombine with and mutate a specific chromosomal locus, such as by insertion into or replacement of the targeted gene.

For targeted gene disruption, a gene targeting vector is made using recombinant DNA techniques and includes 5' and 3' sequences which are homologous to the stem cell endogenous TLR4 gene. The gene targeting vector optionally and preferably further includes a selectable marker such as neomycin phosphotransferase, hygromycin or puromycin. Those of ordinary skill in the art are capable of selecting sequences for inclusion in a gene targeting vector and using these with no more than routine experimentation. Gene targeting vectors can be generated recombinantly or synthetically using well-known methodology.

For methods of DNA injection of a gene targeting vector into a preimplantation embryo, the gene targeting vector is linearized before injection into non-human preimplantation embryos. Preferably, the gene targeting vector is injected into fertilized oocytes. Fertilized oocytes are collected from superovulated females the day after mating (0.5 dpc) and injected with the expression construct. The injected oocytes are either cultured overnight or transferred directly into oviducts of 0.5-day p.c. pseudopregnant females. Methods for superovulation, harvesting of oocytes, gene targeting vector injection and embryo transfer are known in the art and described in Manipulating the Mouse Embryo: A Laboratory Manual, 3rd edition, Cold Spring Harbor Laboratory Press; Dec. 15, 2002, ISBN-10: 0879695919. Offspring can be tested for the presence of TLR4 gene disruption by DNA analysis, such as PCR, Southern blot or sequencing. Mice having disrupted TLR4 gene can be tested for TLR4 protein expression such as by using ELISA or Western blot analysis and/or mRNA expression such as by RT-PCR.

Alternatively the gene targeting vector may be transfected into stem cells (ES cells or iPS cells) using well-known methods, such as electroporation, calcium-phosphate precipitation and lipofection.

Mouse ES cells are grown in media optimized for the particular line. Typically ES media contains 15% fetal bovine serum (FBS) or synthetic or semi-synthetic equivalents, 2 mM glutamine, 1 mM Na Pyruvate, 0.1 mM non-essential amino acids, 50 U/ml penicillin and streptomycin, 0.1 mM 2-mercaptoethanol and 1000 U/ml LIF (plus, for some cell lines chemical inhibitors of differentiation) in Dulbecco's Modified Eagle Media (DMEM). A detailed description is known in the art (Tremml et al., 2008, Current Protocols in Stem Cell Biology, Chapter 1:Unit 1C.4. For review of inhibitors of ES cell differentiation, see Buehr, M., et al. (2003). Genesis of embryonic stem cells. Philosophical Transactions of the Royal Society B: Biological Sciences 358, 1397-1402.

The cells are screened for TLR4 gene disruption by DNA analysis, such as PCR, Southern blot or sequencing. Cells with the correct homologous recombination event disrupting the TLR4 gene can be tested for TLR4 protein expression such as by using ELISA or Western blot analysis and/or mRNA expression such as by RT-PCR. If desired, the selectable marker can be removed by treating the stem cells with Cre recombinase. After Cre recombinase treatment the cells are analyzed for the presence of the nucleic acid encoding TLR4.

Selected stem cells with the correct genomic event disrupting the TLR4 gene can be injected into preimplantation embryos. For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Alternatively to blastocyst injection, stem cells can be injected into early stage embryos (e.g. 2-cell, 4-cell, 8-cell, premorula or morula). Injection may be assisted with a laser or piezo pulses drilled opening the zona pellucida. Approximately 9-10 selected stem cells (ES or iPS cells) are injected per blastocysts, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% $CO_2$, 5% $O_2$ in nitrogen or cultured overnight before transfer into pseudopregnant recipient females. In a further alternative to stem cell injection, stem cells can be aggregated with morula stage embryos. All these methods are well established and can be used to produce stem cell chimeras. For a more detailed description see Manipulating the Mouse Embryo: A Laboratory Manual, 3rd edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259: Method for making genetic modifications, U.S. Pat. No. 7,659,442, U.S. Pat. No. 7,294,754, Kraus et al. 2010, Genesis 48, 394-399).

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation. Chimeric males are selected for breeding. Offspring can be analyzed for transmission of the ES cell genome by coat color and nucleic acid analysis, such as PCR, Southern blot or sequencing. Further the expression of TLR4 can be analyzed for TLR4 mRNA or protein expression such as by protein analysis, e.g. immunoassay, or functional assays, to confirm TLR4 gene disruption. Offspring having the TLR4 gene disruption are intercrossed to create non-human animals homozygous for the TLR4 gene disruption. The transgenic mice are crossed to the immunodeficient mice to create a congenic immunodeficient strain with the TLR4 gene disruption.

Methods of assessing a genetically modified non-human animal to determine whether the toll-like receptor 4 gene is disrupted such that the non-human animal lacks the capacity to express the toll-like receptor 4 gene are well-known and include standard techniques such as nucleic acid assays, spectrometric assays, immunoassays and functional assays.

One or more standards can be used to allow quantitative determination of TLR4 in a sample.

Assays for assessment of function toll-like receptor 4 in an animal having a putative disruption of the TLR4 gene can be performed. Assays for assessment of function toll-like receptor 4 in an animal having a putative disruption of the TLR4 gene are known in the art as exemplified in Deering et al., Clin Vaccine Immunol January 2006, vol. 13, No. 1, 68-76.

The term "wild-type" refers to a naturally occurring or unmutated organism, protein or nucleic acid.

Optionally, genetically modified immunodeficient non-human animals of the present invention are produced by selective breeding. A first parental strain of non-human animal which has a first desired genotype may be bred with a second parental strain of non-human animal which has a second desired genotype to produce offspring which are genetically modified non-human animals having the first and second desired genotypes. For example, a first mouse which is immunodeficient may be bred with a second mouse which has a toll-like receptor 4 gene disruption such that expression of toll-like receptor 4 is absent or reduced to produce offspring which are immunodeficient and have a toll-like receptor 4 gene disruption such that expression of toll-like receptor 4 is absent or reduced. In further examples, a NOD.Cg-Prkdc$^{scid}$Il2rg$^{tm1Wjl}$/SzJ mouse or a NOD.Cg-Rag1tm1Mom Il2rg$^{tm1Wjl}$/SzJ mouse may be bred with a mouse which has a toll-like receptor 4 gene disruption such that expression of toll-like receptor 4 is absent or reduced to produce offspring which are immunodeficient and have a toll-like receptor 4 gene disruption such that expression of toll-like receptor 4 is absent or reduced.

Aspects of the invention provide genetically modified animals that include a toll-like receptor 4 gene disruption in substantially all of their cells, as well as genetically modified animals that include a toll-like receptor 4 gene disruption in some, but not all their cells.

Genetically modified immunodeficient non-human animals of the present invention are preferably non-human mammals, particularly rodents, such as mice, rats or guinea pigs.

A genetically modified immunodeficient mouse having an IL2 receptor gamma chain deficiency in combination with the scid mutation provided according to aspects of the present invention whose genome includes a disrupted toll-like receptor 4 gene such that the mice are incapable of expressing toll-like receptor 4 is a NOD.Cg-Prkdc$^{scid}$Il2rg$^{tm1Wjl}$Tlr4$^{Lps-Del}$/SzJ (NSG-TLR4$^{null}$) mouse.

Methods for producing a non-human animal model system for response of xenogeneic innate immune cells according to aspects of the present invention include providing a genetically modified immunodeficient non-human animal comprising a disrupted toll-like receptor 4 gene such that the genetically modified immunodeficient non-human animal lacks the capacity to express the toll-like receptor 4 gene; and administering xenogeneic stem cells to the genetically modified immunodeficient non-human animal. The immunodeficient non-human animal may have a severe combined immunodeficiency, an IL2 receptor gamma chain deficiency, or a severe combined immunodeficiency and an IL2 receptor gamma chain deficiency in combination.

The term "xenogeneic" is used herein with reference to a host cell or organism to indicate that the material referred to as "xenogeneic" is derived from another species than that of the host cell or organism.

The term "haematopoietic stein cells" as used herein refers to multipotent stem cells functional to give rise to an immune system. Haematopoietic stem cells from mice express c-Kit receptor. C-Kit receptor is well-known in the art, for example as described in Vandenbark G R et al., 1992, Cloning and structural analysis of the human c-kit gene, Oncogene 7(7): 1259-66; and Edling C E, Hallberg B, 2007, c-Kit—a hematopoietic cell essential receptor tyrosine kinase, Int. J. Biochem. Cell Biol. 39(11):1995-8. Human haematopoietic stem cells express CD34. CD34 is a well-known protein, for example as described in Simmons D L et al., Molecular cloning of a cDNA encoding CD34, a sialomucin of human hematopoietic stem cells., J. Immunol. 148 (1): 267-71, 1992.

Methods for producing a mouse model system for response of xenogeneic innate immune cells according to aspects of the present invention include providing a genetically modified immunodeficient mouse comprising a disrupted toll-like receptor 4 gene such that the genetically modified immunodeficient mouse lacks the capacity to express the toll-like receptor 4 gene; and administering xenogeneic stem cells to the genetically modified immunodeficient mouse. The immunodeficient mouse may have a severe combined immunodeficiency, an IL2 receptor gamma chain deficiency, or a severe combined immunodeficiency and an IL2 receptor gamma chain deficiency in combination.

According to aspects of the present invention, xenogeneic haematopoietic stem cells are administered to a genetically modified immunodeficient non-human animal of the present invention comprising a disrupted toll-like receptor 4 gene such that the non-human animal lacks the capacity to express the toll-like receptor 4 gene, wherein the xenogeneic haematopoietic stem cells differentiate into xenogeneic innate immune cells in the genetically modified immunodeficient non-human animal.

According to aspects of the present invention, human haematopoietic stem cells are administered to a genetically modified immunodeficient mouse of the present invention comprising a disrupted toll-like receptor 4 gene such that the mouse lacks the capacity to express the toll-like receptor 4 gene, wherein the human haematopoietic stem cells differentiate into human innate immune cells in the genetically modified immunodeficient mouse.

Hematopoietic stem cells for administration to a genetically modified immunodeficient animal having a disrupted toll-like receptor 4 gene can be obtained from any tissue containing HSC such as, but not limited to, umbilical cord blood, bone marrow, GM-CSF-mobilized peripheral blood and fetal liver.

Optionally, hematopoietic stem cells for administration to a genetically modified immunodeficient animal having a disrupted toll-like receptor 4 gene can be obtained as cells cultured in vitro prior to administration to expand the population of cells obtained from one or more tissues containing HSC such as, but not limited to, umbilical cord blood, bone marrow, GM-CSF-mobilized peripheral blood and fetal liver.

HSC can be administered into newborn animals by administration via various routes, such as, but not limited to, into the heart, liver and/or facial vein. HSC can be administered into adult animals by various routes, such as, but not limited to, administration into the tail vein, into the femur bone marrow cavity or into the spleen. In a further example, the FISC as fetal liver can be engrafted under the renal capsule.

Optionally, FISC are administered to a conditioned animal. Conditioning of a recipient animal in preparation for receipt of HSC is performed to deplete or suppress the HSCs and progenitor cells endogenous to the recipient animal prior to receipt of the xenogeneic HSCs. Conditioning of a recipient animal includes administration of radiation and/or one or more chemical agents effective to deplete or suppress the HSCs and progenitor cells endogenous to the recipient animal prior to receipt of the xenogeneic HSCs. Busulfan is a well-known example of a chemical agent effective to deplete or suppress the HSCs and progenitor cells endogenous to the recipient animal prior to receipt of the xenogeneic HSCs. Conditioning by radiation and/or one or more chemical agents effective to deplete or suppress the HSCs and progenitor cells endogenous to the recipient animal prior to receipt of the xenogeneic HSCs is performed according to well-known protocols to produce a conditioned animal.

Engraftment of xenogeneic HSC can be assessed by any of various methods, such as, but not limited to, flow cytometric analysis of cells in the animals to which the xenogeneic HSC are administered at one or more time points following the administration of HSC.

Exemplary methods for isolation of xenogeneic HSC, administration of the xenogeneic HSC to a host organism and methods for assessing engraftment thereof are described herein and in T. Pearson et al., Curr. Protoc. Immunol. 81:15.21.1-15.21.21, 2008; Ito, M. et al, Blood 100: 3175-3182; Traggiai, E. et al, Science 304: 104-107; Ishikawa, F.

et al, Blood 106: 1565-1573; Shultz, L. D. et al, J. Immunol. 174: 6477-6489; Holyoake T L et al, Exp Hematol., 1999, 27(9):1418-27.

The HSCs administered are isolated from an original source material to obtain a population of cells enriched in HSCs. The isolated HSCs may or may not be pure.

According to aspects, FISCs are purified by selection for a cell marker, such as CD34.

According to aspects, administered human HSCs are a population of human cells in which CD34+ cells constitute about 1-100% of total cells, although a population of human cells in which CD34+ cells constitute fewer than 1% of total cells can be used. According to aspects, administered human HSCs are T cell depleted umbilical cord blood cells in which CD34+ cells make up about 1-3% of total cells, lineage depleted umbilical cord blood cells in which CD34+ cells make up about 50% of total cells, or CD34+ positively selected cells in which CD34+ cells make up about 90% of total cells.

The number of HSCs administered is not considered limiting with regard to generation of a xenogeneic innate immune system in an immunodeficient mouse having a disrupted toll-like receptor 4 gene. A single HSC can generate cells of an immune system. Thus, the number of administered HSCs is generally in the range of $1-1\times10^6$ HSCs where the recipient is a mouse, although more can be used. For other species, the number of cells can be adjusted if necessary using only routine experimentation.

In general, HSCs are present as a subpopulation of CD34+ cells in a larger population of CD34+. Thus, administration of a population of CD34+ cells obtained from any tissue containing HSC such as, but not limited to, umbilical cord blood, bone marrow, GM-CSF-mobilized peripheral blood and fetal liver is administered to deliver the HSC subpopulation to the recipient animal to be engrafted. The number of CD34+ cells obtained from any tissue containing HSC such as, but not limited to, umbilical cord blood, bone marrow, GM-CSF-mobilized peripheral blood and fetal liver administered to deliver the HSC subpopulation to the recipient animal to be engrafted is not limited and can be in the range of 1 cell-1 billion cells, such as 1 cell-500 million cells, 1 cell-100 million cells, 1 cell-10 million cells, 1 cell-5 million cells, 1 cell-1 million cells, 1 cell-500,000 cells, 1 cell-100,000 cells, 1 cell-50,000 cells, 1 cell-10,000 cells, 1 cell-1,000 cells, of such CD34+ cells. Further, the number of CD34+ cells administered is in the range of 100 cells-10 million cells, 100 cells-5 million cells, 100 cells-1 million cells, 100 cells-500,000 cells, 100 cells-100,000 cells, 100 cells-50,000 cells, 100 cells-10,000 cells or 100 cells-1,000 cells. Still further, the number of CD34+ cells administered is in the range of 1000 cells-10 million cells, 1000 cells-5 million cells, 1000 cells-1 million cells, 1000 cells-500,000 cells, 1000 cells-100,000 cells, 1000 cells-50,000 cells or 1000 cells-10,000 cells.

Engraftment is successful where xenogeneic HSCs and cells differentiated from the HSCs in the recipient animal are detected at a time when the majority of any administered non-HSC have degenerated. Detection of differentiated HSC cells can be achieved by detection of xenogeneic DNA in the recipient animal or detection of intact xenogeneic HSCs and cells differentiated from the HSCs, for example. Serial transfer of CD34+ cells into a secondary recipient and engraftment of a xenogeneic hematopoietic system is a further test of HSC engraftment in the primary recipient. Engraftment can be detected by flow cytometry as 0.05% or greater xenogeneic CD45+ cells in the blood at 10-12 weeks after administration of the HSC.

Methods are provided according to aspects of the present invention which include delivery of xenogeneic stem cell factor (SCF) to the xenogeneic hematopoietic stem cells in the immunodeficient animals. The SCF may be delivered acutely or chronically to the animals. According to aspects of the present invention, the immunodeficient non-human animals lacking expression of toll-like receptor 4 further include a transgene encoding a xenogeneic SCF operably linked to a promoter. In a further option, where the animals express the xenogeneic SCF, the animals are not conditioned by administration of a radiomimetic agent prior to administering the xenogeneic stem cells.

Methods for identifying modulators of an innate immune system response according to aspects of the present invention include providing a non-human genetically modified immunodeficient animal comprising a disrupted toll-like receptor 4 gene such that the non-human genetically modified immunodeficient animal lacks the capacity to express the toll-like receptor 4 gene; administering xenogeneic hematopoietic stem cells to the non-human genetically modified immunodeficient animal, wherein the xenogeneic hematopoietic stem cells differentiate to produce xenogeneic innate immune cells in the non-human genetically modified immunodeficient animal; administering an innate immune system stimulator to the animal; administering a test compound to the animal; assaying a response of the xenogeneic innate immune cells to the innate immune system stimulator; and comparing the response to a standard to determine the effect of the test compound on the response of the xenogeneic innate immune cells to the stimulator, wherein an effect of the test substance identifies a modulator of the xenogeneic innate immune system in the animal.

Methods for identifying modulators of an innate immune system response are provided according to the present invention which include providing a non-human genetically modified immunodeficient animal comprising a disrupted toll-like receptor 4 gene such that the non-human genetically modified immunodeficient animal lacks the capacity to express the toll-like receptor 4 gene; administering xenogeneic haematopoietic stem cells to the non-human genetically modified immunodeficient animal, wherein the xenogeneic haematopoietic stem cells differentiate to produce xenogeneic innate immune cells in the non-human genetically modified immunodeficient animal; administering Gram negative bacterial lipopolysaccharides (LPS), Lipid A and/or morphine-3-glucuronide as an innate immune system stimulator to the animal; administering a test compound to the animal; assaying a response of the xenogeneic innate immune cells to the stimulator; and comparing the response to a standard to determine the effect of the test compound on the response of the xenogeneic innate immune cells to the innate immune system stimulator, wherein an effect of the test compound identifies a modulator of the xenogeneic innate immune system in the animal.

According to aspects of methods for identifying modulators of an innate immune system response, the non-human genetically modified immunodeficient animal is a mouse and the xenogeneic haematopoietic stem cells are human haematopoietic stem cells.

According to aspects of methods for identifying modulators of an innate immune system response, the non-human genetically modified immunodeficient animal is a NOD.Cg-Prkdcscid Il2rgtm1 Wjl/SzJ mouse having a disrupted toll-like receptor 4 gene such that the mouse lacks the capacity to express the toll-like receptor 4 gene and the xenogeneic haematopoietic stem cells are human haematopoietic stem cells.

According to aspects of methods for identifying modulators of an innate immune system response, the non-human genetically modified immunodeficient animal is a NOD.Cg-Prkdc$^{scid}$Il2rg$^{tm1Wjl}$Tlr4$^{Lps-Del}$/SzJ (NSG-TLR4$^{null}$) mouse and the xenogeneic haematopoietic stem cells are human haematopoietic stem cells.

A test compound used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these.

Innate immune system stimulators that can be used include, but are not limited to, lipopolysaccharides (LPS), Lipid A and morphine-3-glucuronide.

LPS are obtained commercially or isolated from various Gram negative bacteria, such as *Escherichia coli, Pseudomonas aeruginosa, Klebsiella pneumonia, Salmonella enterica, Salmonella typhosa* and *Serratia marcescens*. LPS is isolated from Gram negative bacteria by well-known methods such as solvent extraction, and maybe purified if desired by standards techniques such as gel filtration chromatography or ion-exchange chromatography.

Portions of LPS can be used, such as Lipid A having 1-6 fatty acyl groups. Lipid A having 1-6 fatty acyl groups may be isolated from bacteria, synthesized, such as monophosphoryl Lipid A or obtained commercially.

Morphine-3-glucuronide is a metabolite of morphine which may be synthesized, isolated or obtained commercially.

A Toll-like receptor 4 agonist is an innate immune system stimulator used in a method according to aspects of the present invention. LPS, Lipid A and morphine-3-glucuronide are non-limiting examples of Toll-like receptor 4 agonists.

Assaying a response of the xenogeneic innate immune cells to the innate immune system stimulator includes assaying one or more indicators of innate immune cell response. Indicators of innate immune cell response to an innate immune system stimulator include, but are not limited to, increased of phenotypic markers and/or cytokines.

Assaying a response of the xenogeneic innate immune cells to the innate immune system stimulator includes assaying one or more indicators of innate immune cell response is performed by methods suitable for detection of changes in levels and/or expression the one or more indicators of innate immune cell response including protein and nucleic acid assays.

The terms "express," "expression," "expressing" and "expresses" with reference to an indicator of innate immune cell response or refer to transcription of the indicator gene to produce a corresponding mRNA and/or translation of the mRNA to produce the functional corresponding protein.

A sample assayed for an indicator of innate immune cell response can be a sample obtained from a non-human animal, illustratively includes spleen, bone marrow, blood, blood plasma and blood serum.

Optionally, particular cell populations of the innate immune system are assayed, such as dendritic cells, plasmacytoid dendritic cells, myeloid dendritic cells, mast cells, monocytes/macrophages, natural killer cells, neutrophils, basophils and eosinophils.

Indicators of human innate immune response include CD80, CD86, IL6, IL8, IL10, TNF and IL1β.

Increased CD80 on CD123+ plasmacytoid dendritic cells (pDC) in a genetically modified mouse of the present invention including human innate immune cells treated with an innate immune system stimulator is indicative of stimulation of the human innate immune system in the mouse.

Increased CD80 on CD11c+ myeloid dendritic cells (mDC) in a genetically modified mouse of the present invention including human innate immune cells treated with an innate immune system stimulator is indicative of stimulation of the human innate immune system in the mouse.

Increased CD80 on CD14+ monocytes/macrophages in a genetically modified mouse of the present invention including human innate immune cells treated with an innate immune system stimulator is indicative of stimulation of the human innate immune system in the mouse.

Increased CD86 on CD123+ plasmacytoid dendritic cells (pDC) in a genetically modified mouse of the present invention including human innate immune cells treated with an innate immune system stimulator is indicative of stimulation of the human innate immune system in the mouse.

Increased CD86 on CD11c+ myeloid dendritic cells (mDC) in a genetically modified mouse of the present invention including human innate immune cells treated with an innate immune system stimulator is indicative of stimulation of the human innate immune system in the mouse.

Increased CD86 on CD14+ monocytes/macrophages in a genetically modified mouse of the present invention including human innate immune cells treated with an innate immune system stimulator is indicative of stimulation of the human innate immune system in the mouse.

Increased human IL6 in a genetically modified mouse of the present invention including human innate immune cells treated with an innate immune system stimulator is indicative of stimulation of the human innate immune system in the mouse.

Increased human IL8 in a genetically modified mouse of the present invention including human innate immune cells treated with an innate immune system stimulator is indicative of stimulation of the human innate immune system in the mouse.

Increased human TNF in a genetically modified mouse of the present invention including human innate immune cells treated with an innate immune system stimulator is indicative of stimulation of the human innate immune system in the mouse.

Increased human IL1β in a genetically modified mouse of the present invention including human innate immune cells treated with an innate immune system stimulator is indicative of stimulation of the human innate immune system in the mouse.

A measured response can be compared to a standard to determine the effect of a test compound on the response of the xenogeneic innate immune cells to the innate immune system stimulator.

Isolated bone marrow cells of genetically modified immunodeficient non-human animals having an engrafted human innate immune system are provided by the present invention, wherein the genetically modified immunodeficient non-human animals have a disrupted toll-like receptor 4 gene such that the genetically modified immunodeficient non-human animals lack the capacity to express the toll-like receptor 4 gene.

Isolated bone marrow cells of genetically modified immunodeficient non-human animals having an engrafted human innate immune system are provided by the present invention, wherein the genetically modified immunodeficient animal is a NOD.Cg-Prkdcscid Il2rgtm1Wjl/SzJ mouse having a disrupted toll-like receptor 4 gene such that the mouse lacks the capacity to express the toll-like receptor 4 gene.

Isolated cells of genetically modified immunodeficient non-human animals are provided by the present invention, wherein the genetically modified immunodeficient non-human animals have a disrupted toll-like receptor 4 gene such that the genetically modified immunodeficient non-human animals lack the capacity to express the toll-like receptor 4 gene.

Isolated cells of genetically modified immunodeficient non-human animals are provided by the present invention, wherein the genetically modified immunodeficient animal is a NOD.Cg-Prkdcscid Il2rgtm1Wjl/SzJ mouse having a disrupted toll-like receptor 4 gene such that the mouse lacks the capacity to express the toll-like receptor 4 gene.

Such isolated cells can be cultured in vitro for use in various assays.

For example, such isolated cells are useful as controls in assays for assessment of a test substance to determine the activity of the test substance as a toll-like receptor 4 agonist or antagonist.

In a further example, such isolated bone marrow cells are useful to determine the activity of the test substance on activity of the innate immune system.

Assays

Binding assays are optionally used in assays according to aspects of the present invention.

A binding assay is an assay in which a target analyte, such as toll-like receptor 4 or an indicator of innate immune cell response, is detected by binding with a binding partner. The term "binding partner" refers to a biological molecule capable of specific binding to a target analyte. Non-limiting examples of binding partners include antibodies, aptamers, receptors, ligands and substrates for enzymatic action of a target analyte. Binding partners may also be nucleic acid probes. The skilled artisan can routinely identify, isolate and/or make binding partners and use them in binding assays. Such techniques are well-known to those of ordinary skill in the art.

A binding assay can be performed according to any of various methods that allow for detection of one or more target analytes by binding to a binding partner. Binding of a target analyte and binding agent can be detected directly or indirectly, such as by use of detectable labels.

Nucleic acid assays such as sequencing, an amplification assay and/or a hybridization assay can be used to detect expression of a target analyte such as toll-like receptor 4 or an indicator of innate immune cell response. Nucleic acid assays, include, but are not limited to, amplification reactions such as polymerase chain reactions (PCR), such as RT-PCR; dot blot; in situ hybridization; Northern blot; and RNase protection. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

A nucleic acid probe or primer able to hybridize to a target analyte mRNA or cDNA to detect and/or quantify mRNA or cDNA can be used in a nucleic assay. A nucleic acid probe can be an oligonucleotide of at least 10, 15, 30, 50 or 100 nucleotides in length and sufficient to specifically hybridize under stringent conditions to a target mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof. The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

A sample from a non-human animal is optionally purified for assay according to a method of the present invention. Methods for isolation of mRNA and/or generation of cDNA for use in an assay of particular sequences are well known in the art.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "amplification assay" refers to a method for copying a template nucleic acid, thereby producing nucleic acids which include copies of all or a portion of the template nucleic acid.

Amplification assays include those which include template directed primer extension catalyzed by a nucleic acid polymerase using a pair of primers which flank the target nucleic acid, illustratively including, but not limited to, polymerase chain reaction (PCR), reverse-transcription PCR (RT-PCR), ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004. The term "primer" refers to a single stranded oligonucleotide, typically about 9-60 nucleotides in length, that may be longer or shorter, and that serves as a point of initiation for template-directed DNA synthesis.

Appropriate reactions conditions for in vitro nucleic acid amplification methods include presence of suitable reaction components including, but not limited to, a polymerase and nucleotide triphosphates. One of skill in the art will be able to determine conditions suitable for amplification of the target nucleic acids with only routine experimentation using primers of the present invention including choice of factors such as buffer, nucleotides, pH, Mg salt concentration, primer concentration and temperature. The nucleic acid product of the amplification methods optionally contains additional materials such as, but not limited to, non-target nucleic acid sequences, functional groups for chemical reaction and detectable labels, present in the primers and not present in the original DNA template. PCR may also being performed as quantitative PCR (Q-PCR) also known as real-time PCR or kinetic PCR (KPCR). Q-PCR is used to amplify and simultaneously quantify a targeted DNA molecule.

The terms "quantitative PCR" or "Q-PCR" refer to a variety of methods for quantifying the results of polymerase chain reactions. Q-PCR methods generally determine or compare the amplification factor, such as determining the threshold cycle (Ct), or are co-amplification methods that compare the amount of produce generated from simultaneous amplification of target and standard templates. Many Q-PCR techniques include reporter probes, intercalator dyes or both. Reporter probes include, but are not limited to, TaqMan® probes (Applied Biosystems), molecular beacons, Scorpion® primers, Lux™ primers and FRET primers; and intercalator dyes include, but are not limited to, ethidium bromide, SYBR® Green I (Molecular Probes) and PicoGreen® (Molecular Probes).

For one or more specific sequences in a DNA sample, Real Time-PCR enables both detection and quantification. The quantity can be either an absolute number of copies or a relative amount when normalized to DNA input or additional normalizing genes. Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target. For example TaqMan probes are used. The TaqMan probe principle relies on the 5'-3" exonuclease activity of Taq polymerase to cleave a dual-labeled probe during hybridization to the complementary target sequence and fluorophore-based detection. As in other real-time PCR methods, the resulting fluorescence signal permits quantitative measurements of the accumulation of the product during the exponential stages of the PCR; however, the TaqMan probe significantly increases the specificity of the detection. TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer) As long as the fluorophore and the quencher are in proximity, quenching inhibits any fluorescence signals.

TaqMan probes are designed such that they anneal within a DNA region amplified by a specific set of primers. As the Taq polymerase extends the primer and synthesizes the nascent strand (again, on a single-strand template, but in the direction opposite to that shown in the diagram, i.e. from 3' to 5' of the complementary strand), the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Hybridization assays for a nucleic acid target include, but are not limited to, dot blot, nucleic acid hybridization, bead assays, in situ hybridization, Northern blot, Southern blot and microarray assays. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

Nucleic acid hybridization assays include use of a nucleic acid probe which specifically hybridizes to a target nucleic acid under defined hybridization and wash conditions. The term "probe" encompasses nucleic acid sequences of various lengths, typically at least about 9 to about 8000 nucleotides in length, but may be shorter or longer as long as the probe is capable of specifically hybridizing to a target nucleic acid in a nucleic acid hybridization assay. A probe may be single or double stranded and may be generated by recombinant methods, chemical synthesis, isolation from natural sources, or a combination of two or more of these.

Immunoassay methods can be used to assay a target analyte such as toll-like receptor 4 or an indicator of innate immune cell response in a sample, including, but not limited to, enzyme-linked immunosorbant assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Onnerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target analyte. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in Antibody Engineering, Kontennann, R. and Dad, S. (Eds.), Springer, 2001; Harlow, E. and Lane, D., Antibodies: A Laboratory Manual, Cold Spring Harbor Laboratory Press, 1988; F. Breitling and S. Dad, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering; Methods and Protocols, Methods in Molecular Biology, Humana Press, 2003; and Kohler, G. and Milstein, C., Nature, 256:495-497 (1975). Antibodies for target analytes, such as toll-like receptor 4 or indicators of innate immune cell response, can be produced in animals, synthesized, produced by recombinant methods and/or obtained commercially.

Aptamers can be used to assay a target analyte. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Detecting binding between a target analyte present in a sample and a binding partner is achieved by any of various methods known in the art, illustratively including detection of a detectable label directly or indirectly attached to the target analyte or the binding partner. The term "detectable label" refers to a material capable of producing a signal indicative of the presence of the detectable label by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, an electron dense particle, a magnetic particle, an enzyme, a substrate, a radioisotope and a chromophore.

The identity of a particular detectable label or labels used depends on the detection process used. Such detection processes are incorporated in particular assay formats illustratively including ELISA, Western blot, immunoprecipitation, immunocytochemistry, immuno-fluorescence assay, liquid chromatography, flow cytometry, other detection processes known in the art, or combinations thereof.

A binding assay can incorporate a binding partner attached to a support. A support with attached binding partner used in a binding assay can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a binding partner can be stably attached for use in a binding assay.

A support used can include functional groups for binding to binding partners, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of binding partners to a support is achieved by any of various methods, illustratively including adsorption and chemical bonding. In one example, 1-Ethyl-3-[3-dimethylaminopropyl]carbodiimide hydrochloride, EDC or EDAC chemistry, can be used to attach binding partners to particles. The binding partners can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: A Comprehensive Introduction, Academic Press, 1997.

Such supports can be in any of a variety of forms and shapes including, but not limited to, microtiter plates, microtiter wells, pins, fibers, beads, slides, silicon chips and membranes such as a nitrocellulose or PVDF membrane.

Any of various spectroscopy methods can be used to assay a target analyte, such as toll-like receptor 4 or an indicator of innate immune cell response, according to aspects of the present invention, including, but not limited to, gas chromatography, liquid chromatography, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

Optionally, spectrometric analysis is used to assay a sample for a target analyte such as toll-like receptor 4 or an indicator of innate immune cell response. Mass analysis can be used in an assay according to aspects of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Standards

Standards suitable for assays are well-known in the art and the standard used can be any appropriate standard.

In one example, a standard is a result of an assay of the one or more indicators of innate immune cell response in a comparable sample from a control animal.

A standard may be a reference level of the one or more indicators of innate immune cell response previously determined in a sample of an individual control animal or in a population of control animals and stored in a print or electronic medium for recall and comparison to a result of an assay of the one or more indicators of innate immune cell response in an animal to which a test compound is administered.

A standard can be a result of an assay of the one or more indicators of innate immune cell response in a comparable sample from an animal at a different time. For example, a standard can be a result of an assay of the one or more indicators of innate immune cell response in a comparable sample obtained from the same animal at a different time, prior to or after administration of the test compound. A first sample can be obtained from an individual animal at a first time to obtain an animal-specific baseline level of the one or more indicators in the first sample. A second sample can be obtained from the individual animal at a second time and assayed for the one or more indicators to monitor differences in the levels of the one or more indicators compared to the first sample. Additional samples can be obtained from the animal at additional time points and assayed for the one or more indicators to monitor differences in the levels of the one or more indicators compared to the first sample, second sample or other samples.

A standard can be an average level of one or more indicators in comparable samples obtained from one or more populations. The "average level" is determined by assay of the one or more indicators in comparable samples obtained from each animal of the population. The term "comparable sample" is used to indicate that the samples are of the same type, i.e. each of the comparable samples is a serum sample, for example.

A difference detected in levels or expression of one or more target analytes in assays of the present invention compared to a standard can be an increase or decrease in level or expression of the one or more target analytes. The magnitude of the increase or decrease can be, for example, at least 5%, 10%, 15%, 20%, 25%, 30%, 35%, 40%, 45%, 50%, 55%, 60%, 65%, 70%, 75%, 80%, 85%, 90%, 95%, 99%, or more, of the standard level.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

Aspects of inventive genetically modified non-human animals, compositions and methods are illustrated in the following examples. These examples are provided for illustrative purposes and are not considered limitations on the scope of inventive compositions and methods.

EXAMPLES

Mice

NOD.Cg-Prkdc$^{scid}$Il2rg$^{tm1Wjl}$/SzJ (NOD-scid IL2rγ$^{null}$, NSG) mice and NOD.Cg-Prkdc$^{scid}$Il2rg$^{tm1Wjl}$Tlr4$^{Lps-Del}$ (NSG-TLR4$^{null}$) mice, which do not express murine TLR4, were obtained from colonies developed and maintained at The Jackson Laboratory (Bar Harbor, Me.). NOD/Lt-Tlr4$^{Lps-Del}$ mice are described in Wen et al., Nature, 455: 1109-1113, 2008. NSG mice lacking TLR4 were generated by first crossing NOD/Lt-Tlr4$^{Lps-Del}$ mice with NSG mice. Further backcrosses of the F1 offspring to NSG mice were carried out to fix the Prkdc$^{scid}$ and Il2rg$^{tm1Wjl}$ mutations to homozygosity. The NOD.Cg-Prkdc$^{scid}$Il2rg$^{tm1Wjl}$Tlr4$^{Lps-Del}$/SzJ (NSG-TLR4$^{null}$) mice were maintained by matings of homozygote siblings. All animals were housed in a specific pathogen free facility, in microisolator cages, and given autoclaved food and maintained on sulfamethoxazole-trimethoprim medicated water (Goldline Laboratories, Ft. Lauderdale, Fla.) and acidified autoclaved water on alternating weeks.

Engraftment of Mice with Human Hematopoietic Stem Cells

Groups of 24 to 72 hour-old (newborn) NSG and NSG-TLR4$^{null}$ mice were irradiated with 100cGy as described in Pearson et al., 2008. Irradiated mice were injected with CD3 T cell-depleted human umbilical cord blood (UCB) containing $3 \times 10^4$ CD34$^+$ hematopoietic stem cells (HSC) in a 25-50 µL volume via intracardiac injection as described in Brehm et al., 2010. After 12 weeks, flow cytometry analyses of the blood of HSC recipients quantified the engraftment of the human immune system. For experimental studies only mice with >10% peripheral human CD45+ cells and >5% human CD3+ T cells were used.

Antibodies and Flow Cytometry

For analysis of mouse innate immune cells, monoclonal antibodies specific for mouse CD45 (30-F11), PDCA1 (927), CD11c (N418), CD11b (M1/70), CD40 (3/23) and CD86 (GL1) were purchased from BD Biosciences, Inc. (San Jose, Calif.), eBiosciences (San Diego, Calif.) or BioLegend, (San Diego, Calif.). For analysis of human hematopoietic engraftment, monoclonal antibodies specific for human CD45 (2D1), CD3 (UCHT1), CD4 (RPA-T4), CD8 (RPA-T8), CD11c (B-ly6), CD14 (HCD14), CD20 (2H7) and CD80 (2D10), CD86 (2331) and CD123 (AC145) were purchased from BD Biosciences, Inc., eBiosciences or BioLegend. Single-cell suspensions of bone marrow (BM) and spleen were prepared from engrafted mice, and whole blood was collected in heparin. Single cell suspensions of $1 \times 10^6$ cells in 50 µL or 100 µL of whole blood were washed with FACS buffer (PBS supplemented with 2% fetal bovine serum, (HyClone, Logan, Utah) and 0.02% sodium azide (Sigma, St. Louis, Mo.)) and then pre-incubated with rat anti-mouse FcR11b (clone 2.4G2, BD Biosciences) to block Fc binding. Specific antibodies were then added to the samples and incubated for 30 min at 4° C. Stained samples were then washed and fixed with 2% paraformaldehyde for cell suspensions or treated with BD FACS lysing solution for whole blood. At least 50,000 events were acquired on LSRII or FACSCalibur instruments (BD Biosciences). Data analysis was performed with FlowJo (Tree Star, Inc., Ashland, Oreg.) software.

LPS and poly(I:C) Treatment

Ultra Pure lipopolysaccharide (LPS, *E. coli* 0111:B4 strain), and polyinosinic-polycytidylic (poly(I:C), high molecular weight, HMW) were purchased from Invivogen (San Diego, Calif.). The indicated mice were injected intraperitoneally (IP) with 100 µg of either LPS or poly(I:C).

Serum Cytokine Analysis

Levels of murine IL6, IL10, monocyte chemoattractant protein-1 (MCP1), TNF, and IL12p70 were determined in the serum from the indicated mice using the BD™ Cytometric Bead Array (CBA) Mouse Inflammation Kit. Levels of human IL8, IL1β, IL6, IIL10, TNF, and IL12p70 were determined in the serum from the indicated mice using the BD™ CBA Human Inflammation Kit.

Statistical Analyses

To compare individual pair-wise groupings, unpaired t-tests and Mann-Whitney test for parametric and non-parametric data, respectively, were used. Three or more means were compared by one-way ANOVA and the Bonferroni multiple comparison test. Significant differences were assumed for p values<0.05. Statistical analyses were performed using GraphPad Prism software (version 6.0, GraphPad, San Diego, Calif.).

Comparison of Mouse Innate Immune System Development in NSG and NSG-TLR4$^{null}$ Mice NSG mice lack T cells, B cells and NK cells but still maintain components of the innate immune system, including dendritic cells and macrophages Shultz et al., 2005. The percentages and total number of mouse innate immune cell populations in the spleen and bone marrow (BM) of 8 to 12 week old NSG mice and NSG-TLR4$^{null}$ mice were analyzed and results are shown in FIGS. 1A-1D. Mouse PDCA1+ (CD317) plasmacytoid dendritic cells, CD11c+/CD11b− dendritic cells, CD11c+CD11b+ dendritic cells, and CD11c−/CD11b+ macrophages were identified by flow cytometric analysis. The data are representative of 3 independent experiments. Total Number of mice N=15 The percentages (FIGS. 1A and 1C) and total number (FIGS. 1B and 1D) of mouse innate immune cells in spleen (FIGS. 1A and 1B) and bone marrow (FIGS. 1C and 1D) were comparable for NSG and NSG-TLR4$^{null}$ mice, with minor statistically significant differences observed. For example, NSG-TLR4$^{null}$ mice have lower levels of plasmacytoid DC in spleen and bone marrow as compared to NSG mice, while slightly higher levels of CD11b+ macrophages were detected in the spleens of NSG-TLR4$^{null}$ mice. These results demonstrate that the TLR4 mutation results in minor differences in dendritic cell populations and macrophages in NSG mice, but overall there are not major quantitative changes in these innate immune cell populations.

To confirm that NSG-TLR4$^{null}$ mice are unable to respond to TLR4 agonists, NSG and NSG-TLR4$^{null}$ mice were treated with LPS and the ability of innate immune cells to increase expression of phenotypic markers (Table I) and produce cytokines (FIG. 2) was evaluated. To assess phenotypic changes on mouse innate immune cells, NSG and NSG-TLR4$^{null}$ mice were administered 100 µg of either LPS or poly(I:C) by intraperitoneal (IP) injection, and 24 hours later expression of CD40 and CD86 was evaluated on the surface of dendritic cells and macrophages recovered from the spleen as shown in Table I.

LPS treatment of NSG mice stimulated increased expression of CD40 on CD11c+/CD11b− DC, CD11c+/CD11b+ DC and CD11c−/CD11b+ macrophages and increased expression of CD86 on CD11c+/CD11b− DC as compared to control mice. In contrast, LPS treatment of NSG-TLR4$^{null}$ mice did not stimulate changes in the expression of CD40 and CD86 on mouse innate immune cell populations. Poly(I:C)-induced increases in the expression of CD40 and CD86 on mouse innate immune cells was similar between NSG and NSG-TLR4$^{null}$ mice.

To assess cytokine production, mice were injected IP with 100 µg of either LPS or poly(I:C), and 24 hours later serum was collected and cytometric bead array (CBA) assays performed, results of which are shown in FIG. 2. Serum samples were evaluated for mouse IL-6, IL-10, MCP1, IFNγ, TNF and IL12p70 and compared to mice injected IP with phosphate buffered saline (PBS). The cytokine levels shown are an average of 6 mice and error bars indicate the standard error of mean. The data are representative of 3 independent experiments. For statistical analysis, the average cytokine levels for LPS and poly(I:C) treated mice were compared to levels for PBS treated mice;  $p<0.01$, * $p<0.001$, **** $p<0.0001$. NSG mice produced significant levels of IL-6, IL-10 and MCP following challenge with LPS and this cytokine response was absent in NSG-TLR4$^{null}$ mice treated with LPS. Poly(I:C) treatment induced a similar mouse cytokine response in both NSG and NSG-TLR4$^{null}$ mice. Together these data show that NSG-TLR4$^{null}$ mice develop mouse innate immune cells but these cells are unable to mount a functional response to the TLR4 agonist, LPS.

Human immune cell chimerism levels are similar in HSC-engrafted NSG-TLR4$^{null}$ and NSG Mice Human HSC were administered to NSG-TLR4$^{null}$ mice to determine if these mice can engraft human HSC and develop a human immune system to the same level as NSG mice. For these experiments newborn conditioned NSG or NSG-TLR4$^{null}$ mice were engrafted with human HSC as described herein and were evaluated for human cell chimerism in the spleen, bone marrow and blood at 16 weeks by flow cytometry, results of which are shown in FIGS. 3A-3E. The percentages (A, B and C) and total number (D and E) of human CD45+ cells are shown and each point represents an individual animal. The data are from a total of 4 independent experiments. Slightly higher percentages of human CD45+ cells were detected in the spleen (FIG. 3A), bone marrow (FIG. 3B) and blood (FIG. 3C) of NSG-TLR4$^{null}$ mice but this was not significantly different from the levels in NSG

TABLE I

Mouse innate immune cells from NSG-TLR4$^{null}$ mice do not increase CD40 or CD86 expression following exposure to LPS.

| | NSG | | | NSG-TLR4$^{null}$ | | |
|---|---|---|---|---|---|---|
| | Control[a] | LPS Treated | poly(IC) Treated | Control | LPS Treated | poly(IC) Treated |
| CD40 Expression | | | | | | |
| CD11c+/CD11b− DC | 6766 ± 753 | 22170 ± 3076[b] | 19935 ± 1020[b] | 6681 ± 530 | 6925 ± 430 | 16160 ± 3782[b] |
| CD11c+/CD11b+ DC | 716.3 ± 101 | 6087 ± 1099[b] | 6860 ± 1276[b] | 737.7 ± 69.8 | 779.3 ± 174 | 5035 ± 3278[b] |
| CD11b+ Macrophage | 4141 ± 404 | 6043 ± 517[b] | 3909 ± 377 | 4593 ± 222 | 4491 ± 205 | 4168 ± 104 |
| CD86 Expression | | | | | | |
| CD11c+/CD11b− DC | 367.3 ± 67.8 | 1005 ± 71.7[c] | 1111 ± 141[c] | 368 ± 70 | 407.3 ± 120.8 | 1315 ± 82[b] |
| CD11c+/CD11b+ DC | 161.3 ± 16.3 | 188.7 ± 29 | 540.3 ± 40[b] | 196.5 ± 25.6 | 169.8 ± 12.7 | 635 ± 57.7[b] |
| CD11b+ Macrophage | 95.98 ± 13.3 | 24.07 ± 9.84 | 68.27 ± 5.93 | 110.85 ± 19.1 | 88.5 ± 11 | 77.77 ± 15.96 |

[a]Control animals were treated with PBS and injected with a volume equal to that used for LPS and poly(IC) injection.
[b]p < 0.001, as compared to untreated
[c]p < 0.01, as compared to untreated mice. There were no significant differences in the number of human CD45+ cells in the spleen (FIG. 3D) and bone marrow (FIG. 3E) of NSG-TLR4$^{null}$ mice as compared to NSG mice.

NSG-TLR4$^{null}$ mice engrafted with human HSC develop human T and B cell populations The levels of human T cells and B cells in spleen, bone marrow and blood of NSG and NSG-TLR4$^{null}$ mice engrafted with human HSC were compared using flow cytometry for levels of human T cells and B cells in the spleen, bone marrow and blood at 16 weeks of age. and results of this comparison are shown in FIGS. 4A-4I. No significant differences were observed for the percentages of human CD3+ T cells (FIGS. 4A, 4B and 4C), the CD4:CD8 T cell ratio (FIGS. 4D, 4E and 4F) or in the percentages of human CD20+ B cells (FIGS. 4G, 4H and 4I) between the HSC engrafted strains. Each point represents an individual animal, and the data are from a total of 4 independent experiments.

Figures 5A, 5B, 5C:
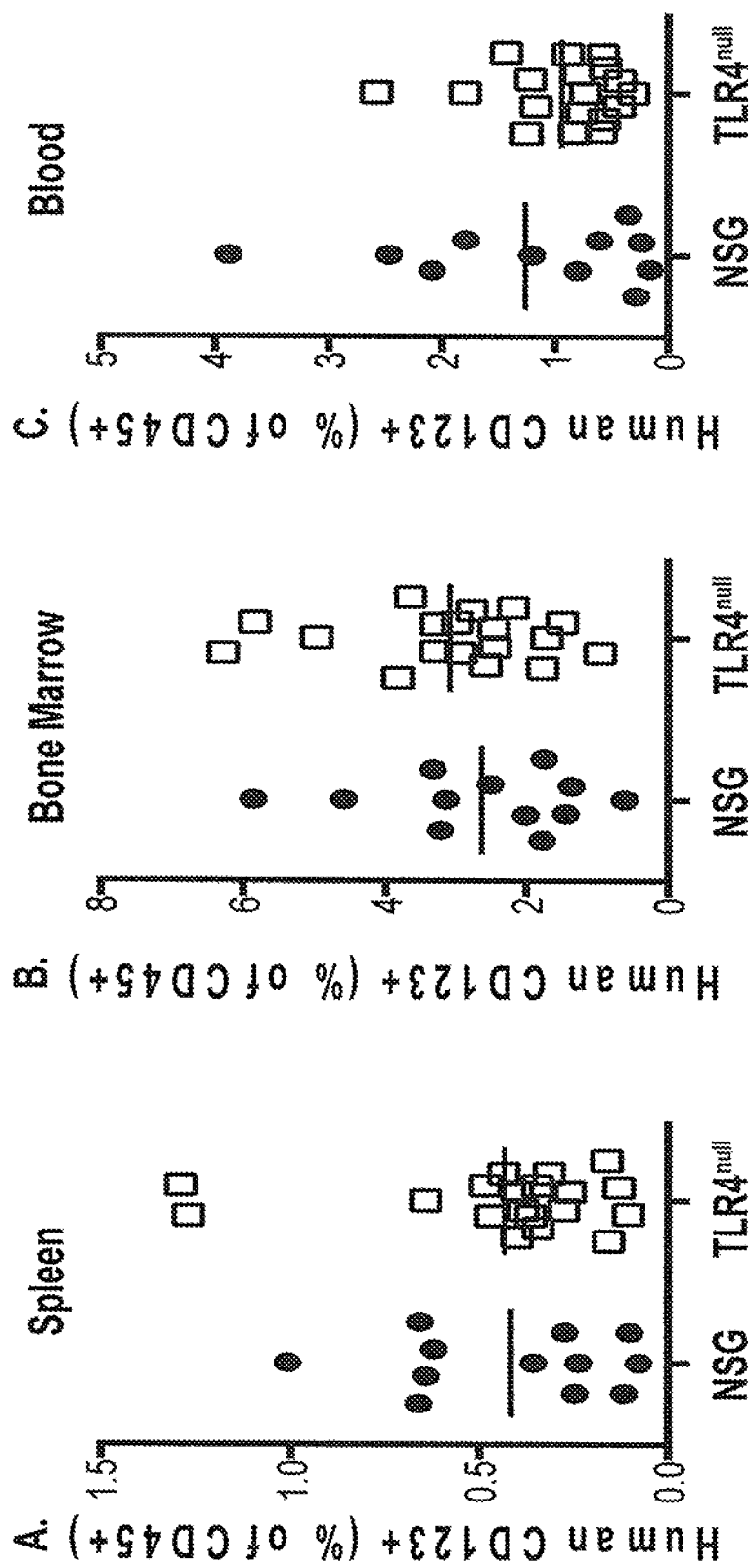
FIG. 5A is a graph showing the percentage of human CD123+ cells in the spleen of NSG or NSG-TLR4$^{null}$ mice engrafted with human HSC 16 weeks prior to analysis.
FIG. 5B is a graph showing the percentage of human CD123+ cells in the bone marrow of NSG or NSG-TLR4$^{null}$ mice engrafted with human HSC 16 weeks prior to analysis.
FIG. 5C is a graph showing the percentage of human CD123+ cells in the blood of NSG or NSG-TLR4$^{null}$ mice engrafted with human HSC 16 weeks prior to analysis.
Figures 5D, 5E, 5F:
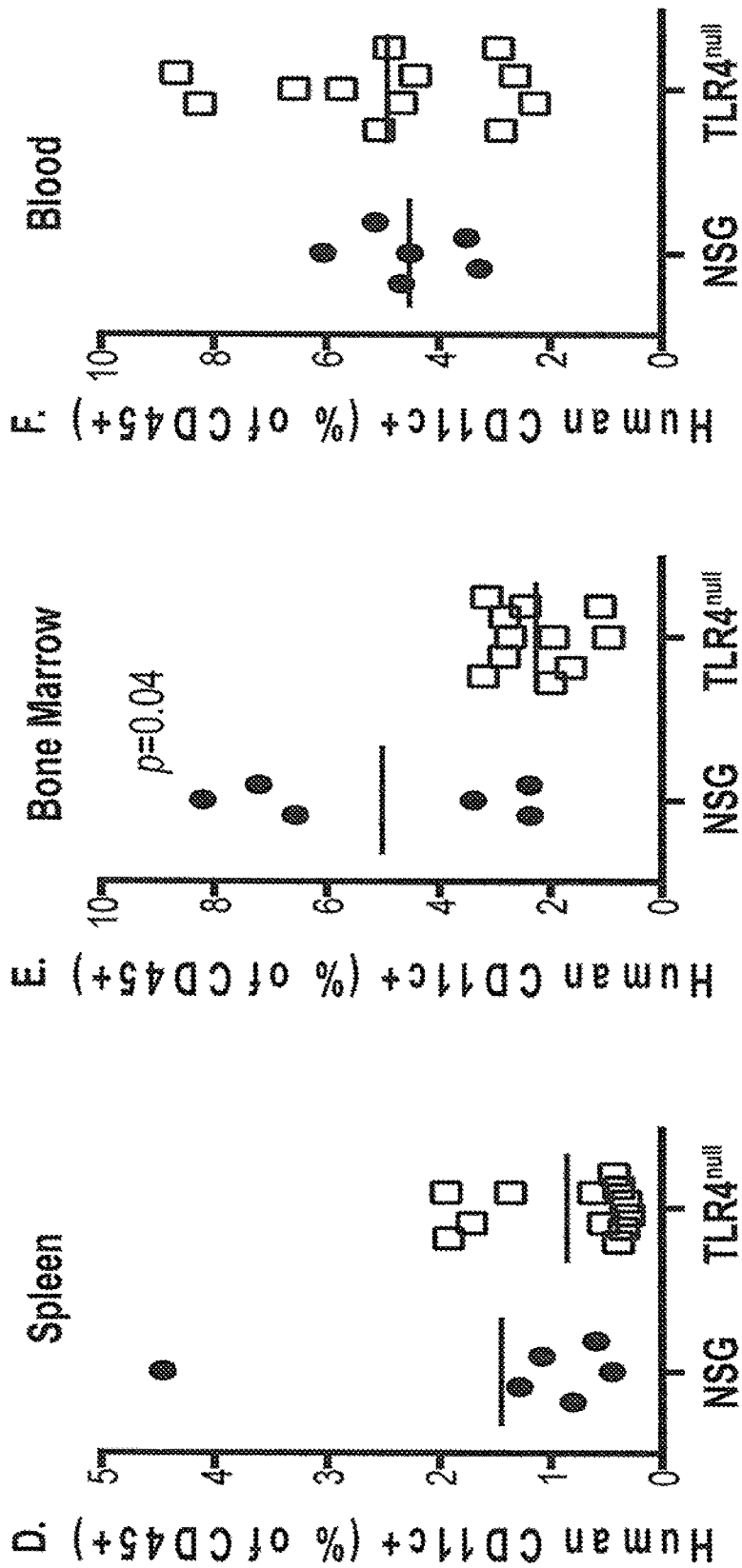
FIG. 5D is a graph showing the percentage of human CD11c+ cells in the spleen of NSG or NSG-TLR4$^{null}$ mice engrafted with human HSC 16 weeks prior to analysis.
FIG. 5E is a graph showing the percentage of human CD11c+ cells in the bone marrow of NSG or NSG-TLR4$^{null}$ mice engrafted with human HSC 16 weeks prior to analysis.
FIG. 5F is a graph showing the percentage of human CD11c+ cells in the blood of NSG or NSG-TLR4$^{null}$ mice engrafted with human HSC 16 weeks prior to analysis.
Figures 5G, 5H, 5I:
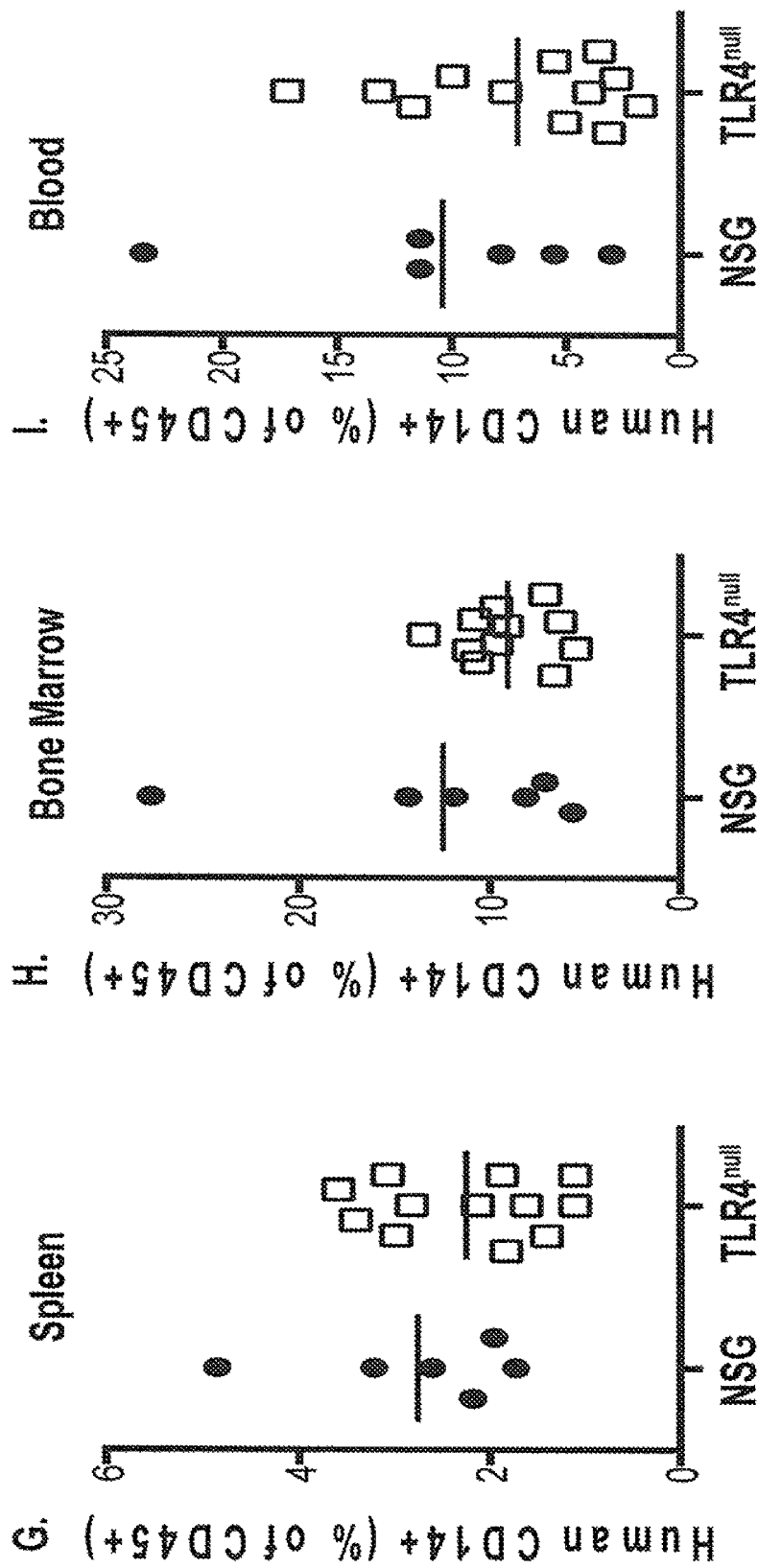
FIG. 5G is a graph showing the percentage of human CD14+ in the spleen of NSG or NSG-TLR4$^{null}$ mice engrafted with human HSC 16 weeks prior to analysis.
FIG. 5H is a graph showing the percentage of human CD14+ cells in the bone marrow of NSG or NSG-TLR4$^{null}$ mice engrafted with human HSC 16 weeks prior to analysis.
FIG. 5I is a graph showing the percentage of human CD4+ cells in the blood of NSG or NSG-TLR4$^{null}$ mice engrafted with human HSC 16 weeks prior to analysis.

The development of human plasmacytoid DC (pDC), human myeloid DC (mDC), and human monocyte/macrophage levels in spleen, BM and blood of NSG and NSG-TLR4$^{null}$ mice engrafted with human HSC was evaluated by flow cytometry for levels of human innate immune cells in the spleen, bone marrow and blood at 16 weeks of age and results are shown in FIGS. 5A-5I. No significant differences were observed for the percentages of human CD123+ pDC cells (FIGS. 5A, 5B and 5C) and human CD14 positive monocyte/macrophage (FIGS. 5G, 5H and 5I) between the HSC engrafted strains. Each point represents an individual animal, and the data are from a total of 4 independent experiments. A significantly higher frequency of human CD11c+ mDC were detected in the BM (FIG. 5E) of NSG-TLR4$^{null}$ mice but no differences were observed in the spleen (FIG. 5D) or blood (FIG. 5F). Overall these data indicate that NSG-TLR4$^{null}$ mice engraft efficiently with human HSC as compared to NSG mice and develop both adaptive and innate human immune cells.

Figures 6A, 6B, 6C:
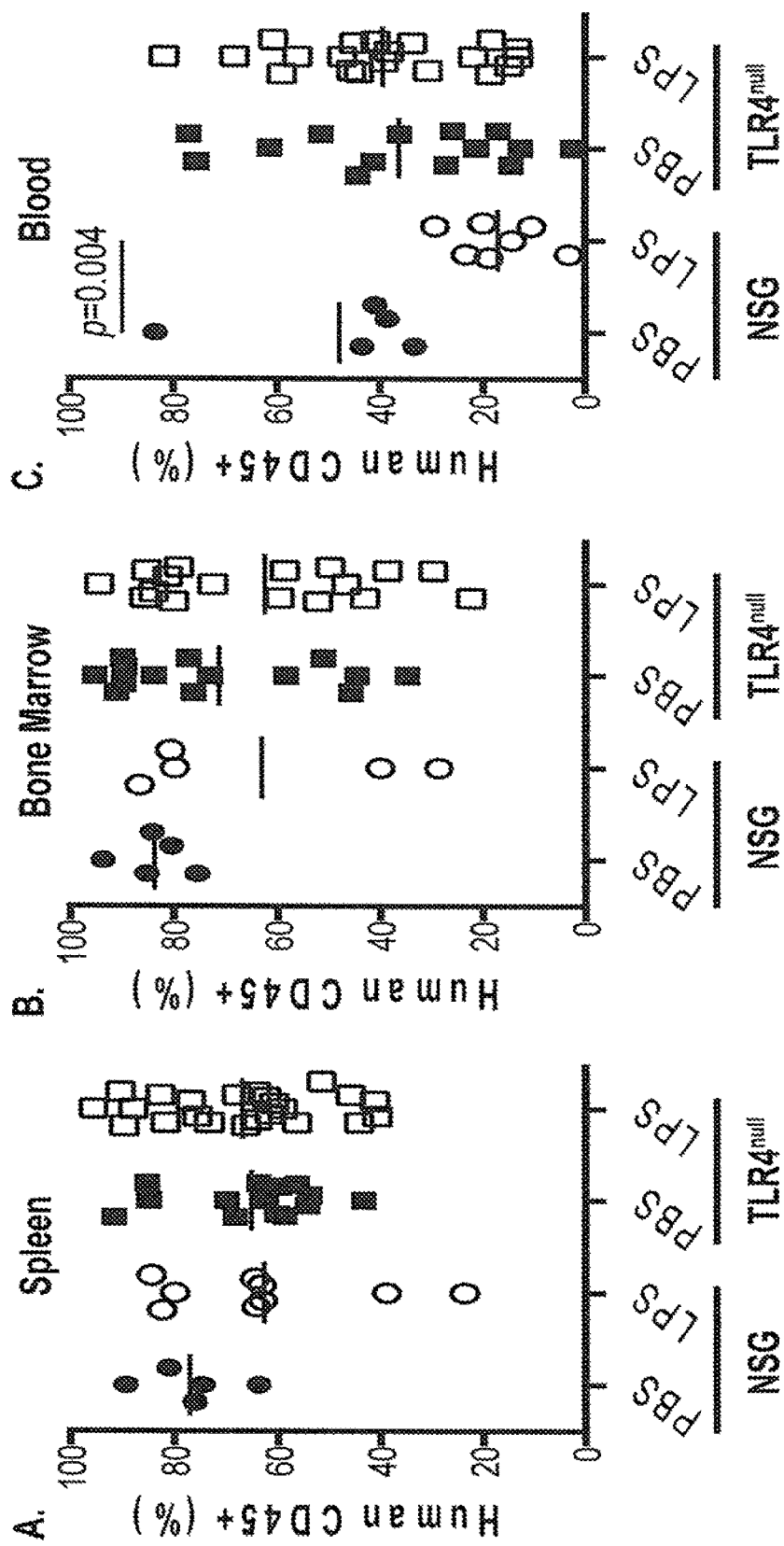
FIG. 6A is a graph showing the percentage of human CD45+ cells in the spleen of newborn conditioned NSG or NSG-TLR4$^{null}$ mice where both types of mice were engrafted with human HSC, and 24 hours after the mice were injected IP with either LPS or phosphate buffered saline (PBS)
FIG. 6B is a graph showing the percentage of human CD45+ cells in the bone marrow of newborn conditioned NSG or NSG-TLR4$^{null}$ mice where both types of mice were engrafted with human HSC, and 24 hours after the mice were injected IP with either LPS or phosphate buffered saline (PBS)
FIG. 6C is a graph showing the percentage of human CD45+ cells in the blood of newborn conditioned NSG or NSG-TLR4$^{null}$ mice where both types of mice were engrafted with human HSC, and 24 hours after the mice were injected IP with either LPS or phosphate buffered saline (PBS)
Figures 6D, 6E, 6F:
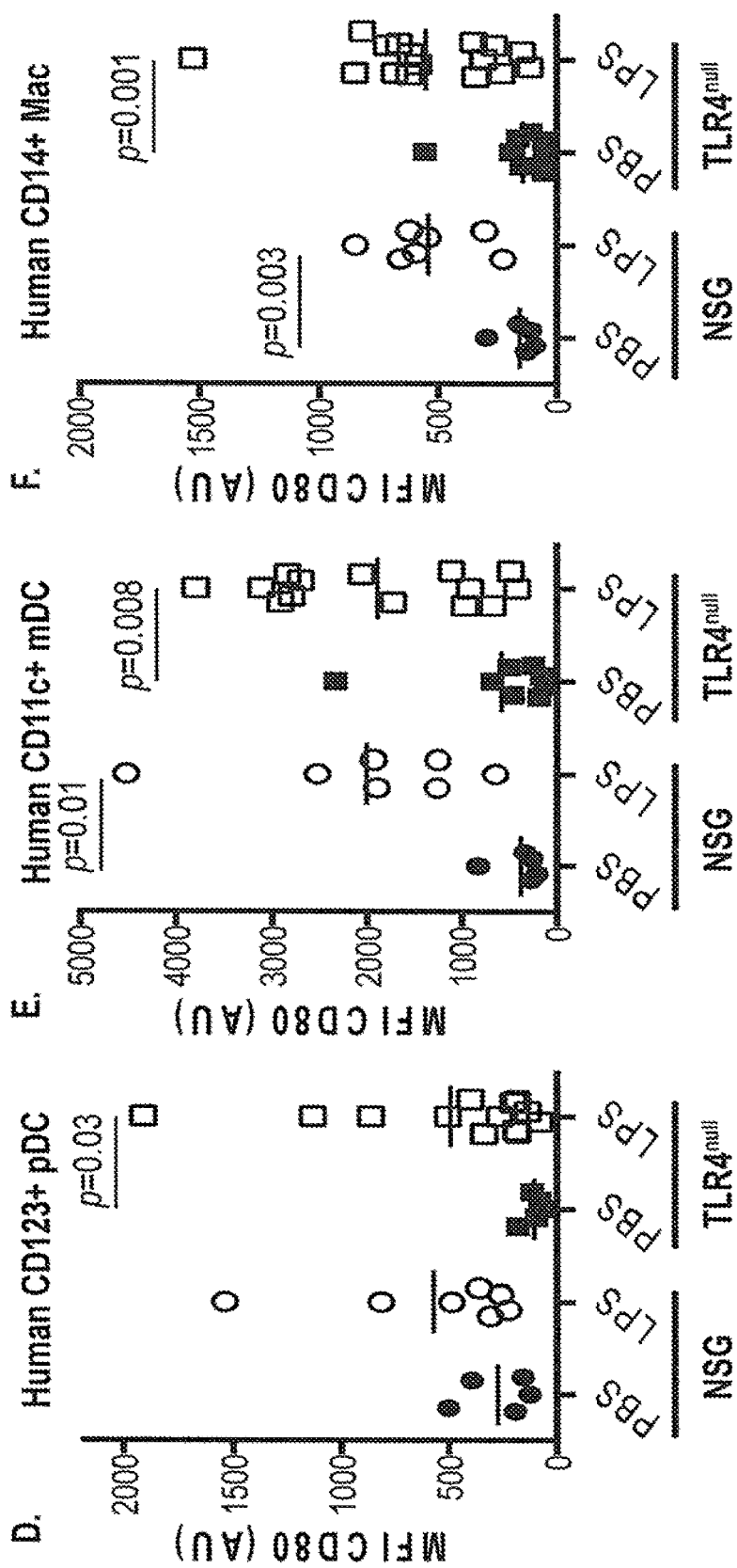
FIG. 6D is a graph showing expression of CD80 in human innate immune cell population pDC from the blood of HSC-engrafted NSG and NSG-TLR4$^{null}$ mice at 24 hours after LPS or PBS treatment.
FIG. 6E is a graph showing expression of CD80 in human innate immune cell population mDC from the blood of HSC-engrafted NSG and NSG-TLR4$^{null}$ mice at 24 hours after LPS or PBS treatment.
FIG. 6F is a graph showing expression of CD80 in human innate immune cell population monocyte/macrophage (Mac) from the blood of HSC-engrafted NSG and NSG-TLR4$^{null}$ mice at 24 hours after LPS or PBS treatment.
Figures 6G, 6H, 6I:
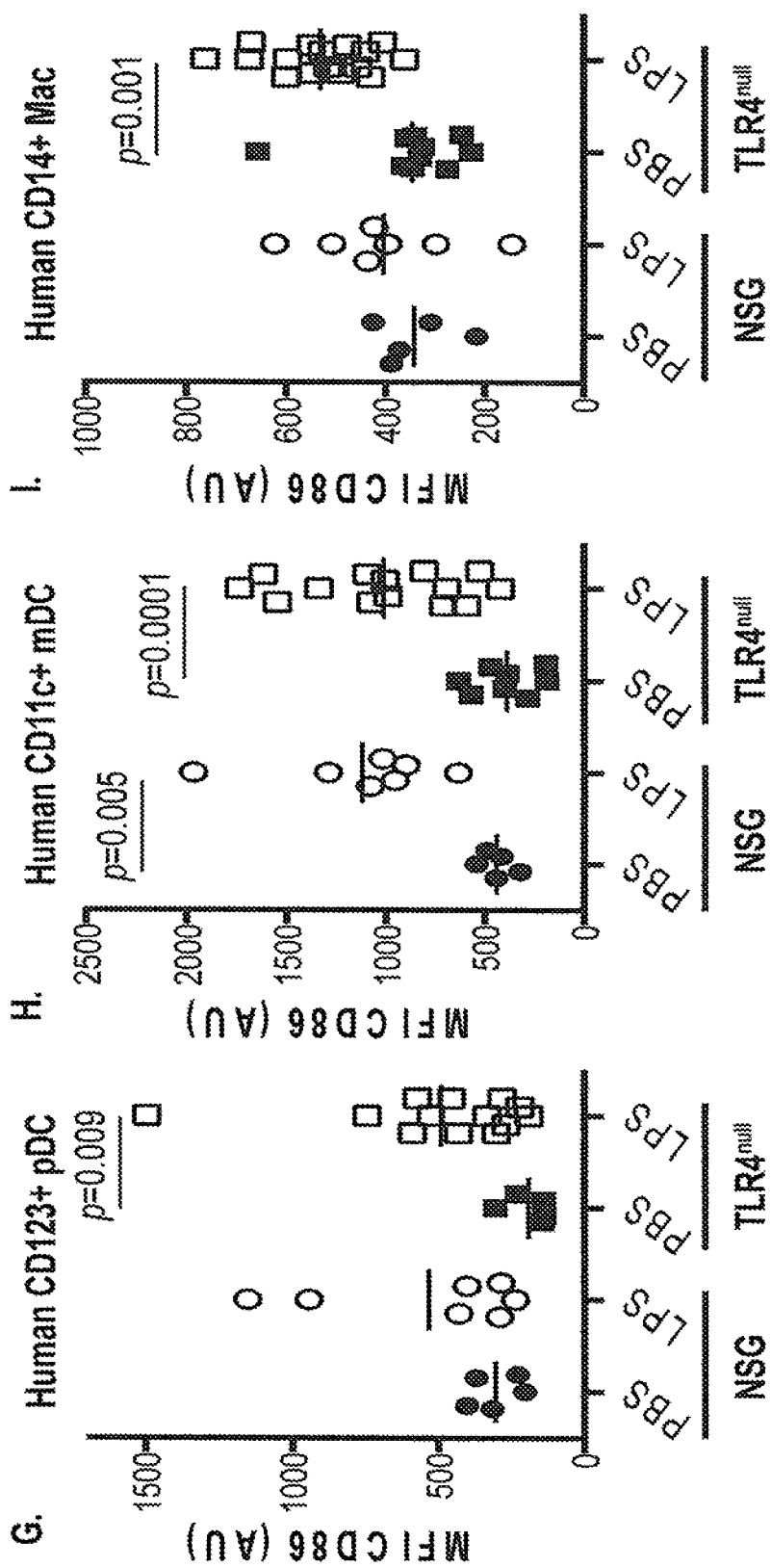
FIG. 6G is a graph showing expression of CD86 in human innate immune cell population pDC from the blood of HSC-engrafted NSG and NSG-TLR4$^{null}$ mice at 24 hours after LPS or PBS treatment.
FIG. 6H is a graph showing expression of CD86 in human innate immune cell population mDC from the blood of HSC-engrafted NSG and NSG-TLR4$^{null}$ mice at 24 hours after LPS or PBS treatment.
FIG. 6I is a graph showing expression of CD86 in human innate immune cell population monocyte/macrophage (Mac) from the blood of HSC-engrafted NSG and NSG-TLR4$^{null}$ mice at 24 hours after LPS or PBS treatment.

LPS treatment activates human innate immune cells in NSG-TLR4$^{null}$ mice engrafted with human HSC The lack of a mouse innate immune response to LPS in NSG-TLR4$^{null}$ mice enables the study of human-specific TLR4-mediated responses in HSC-engrafted mice. The response to LPS treatment of human cells in newborn NSG and NSG-TLR4$^{null}$ mice engrafted with human HSC was compared. HSC-engrafted NSG and NSG-TLR4$^{null}$ mice were treated with PBS or LPS, and 24 hours later the levels of human CD45+ cells were determined in the spleen, BM and blood. No significant differences were detected in the percentage of human CD45+ cells from the spleen (FIG. 6A) and BM (FIG. 6B) for either mouse strain. In contrast, HSC-engrafted NSG mice showed a significant decrease in human CD45+ cells in the blood after LPS treatment and this effect was absent in the NSG-TLR4$^{null}$ mice (FIG. 6C). Human innate immune cell populations (pDC, mDC and monocyte/macrophage) from the blood of HSC-engrafted NSG and NSG-TLR4$^{null}$ mice were analyzed for changes in the expression of CD80 (FIGS. 6D, 6E and 6F) and CD86 (FIGS. 6G, 6H and 6I) at 24 hours after LPS treatment. Treatment of HSC-engrafted NSG-TLR4$^{null}$ mice with LPS stimulated a significant increase in the expression of CD80 and CD86 on human CD123+ pDC (FIGS. 6D, 6G), human CD11c+ mDC (FIGS. 6E, 6H) and human CD14+ monocyte/macrophage (FIGS. 6F, 6I). LPS treatment of HSC-engrafted NSG mice stimulated a significant increase in CD80 expression on human mDC (FIG. 6E) and human monocyte/macrophage (FIG. 6F) and a significant increase in CD86 expression on mDC (FIG. 6H). Each point in FIGS. 6A-6I represents an individual animal, and the data are from a total of 3 independent experiments. These data indicate that the LPS induces more global changes in phenotypic markers on human innate immune cells in HSC-engrafted NSG-TLR4$^{null}$ mice than in NSG mice.

Figures 7A, 7B:
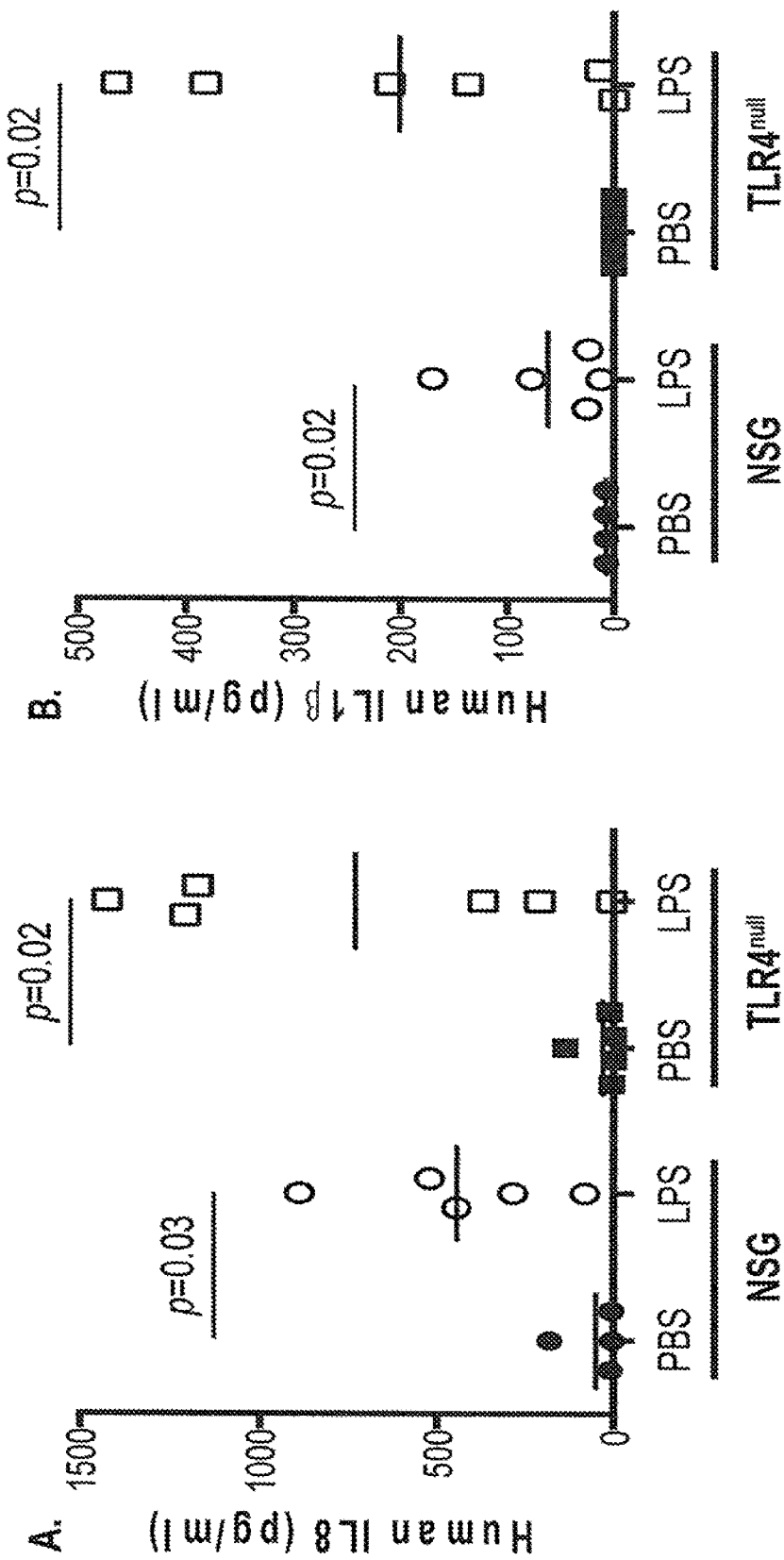
FIG. 7A is a graph showing results of an assay for human IL8 in serum samples from HSC-engrafted NSG and NSG-TLR4$^{null}$ mice at 6 hours after LPS or PBS treatment.
FIG. 7B is a graph showing results of an assay for human IL1β in serum samples from HSC-engrafted NSG and NSG-TLR4$^{null}$ mice at 6 hours after LPS or PBS treatment.
Figure 7D:
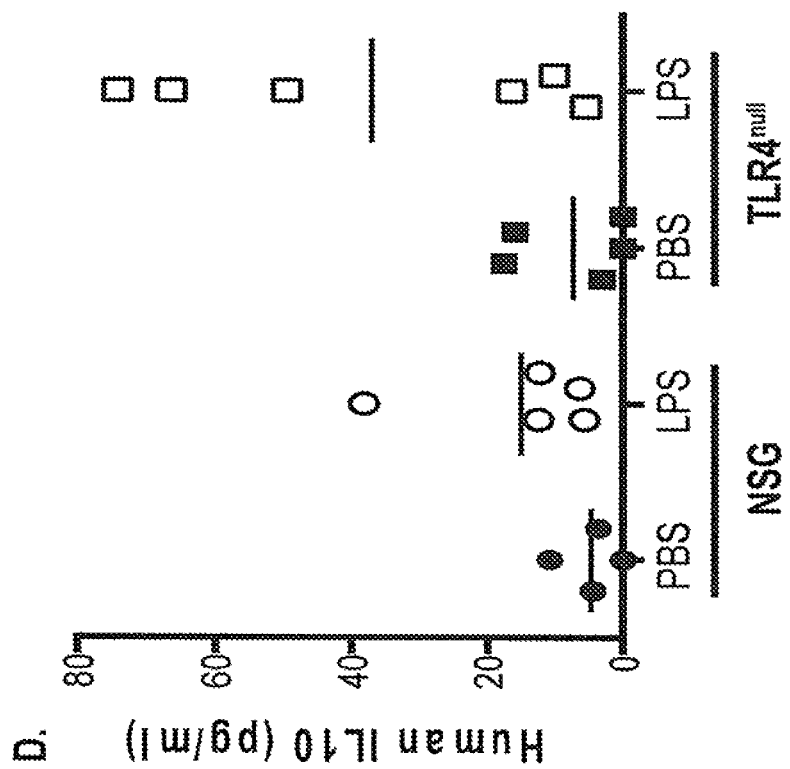
FIG. 7D is a graph showing results of an assay for human IL10 in serum samples from HSC-engrafted NSG and NSG-TLR4$^{null}$ mice at 6 hours after LPS or PBS treatment.
Figure 7C:
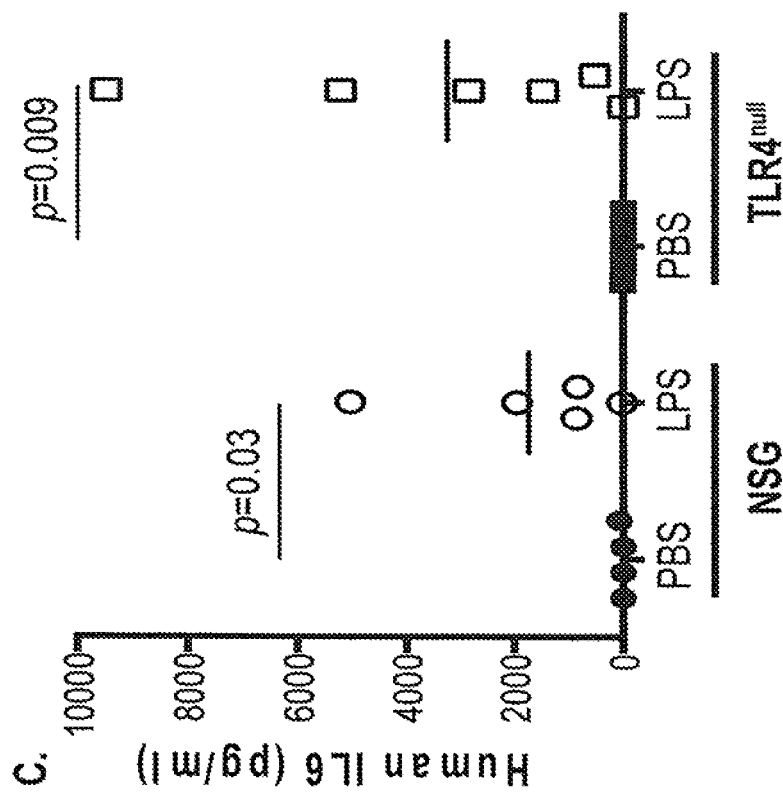
FIG. 7C is a graph showing results of an assay for human IL6 in serum samples from HSC-engrafted NSG and NSG-TLR4$^{null}$ mice at 6 hours after LPS or PBS treatment.
Figure 7F:
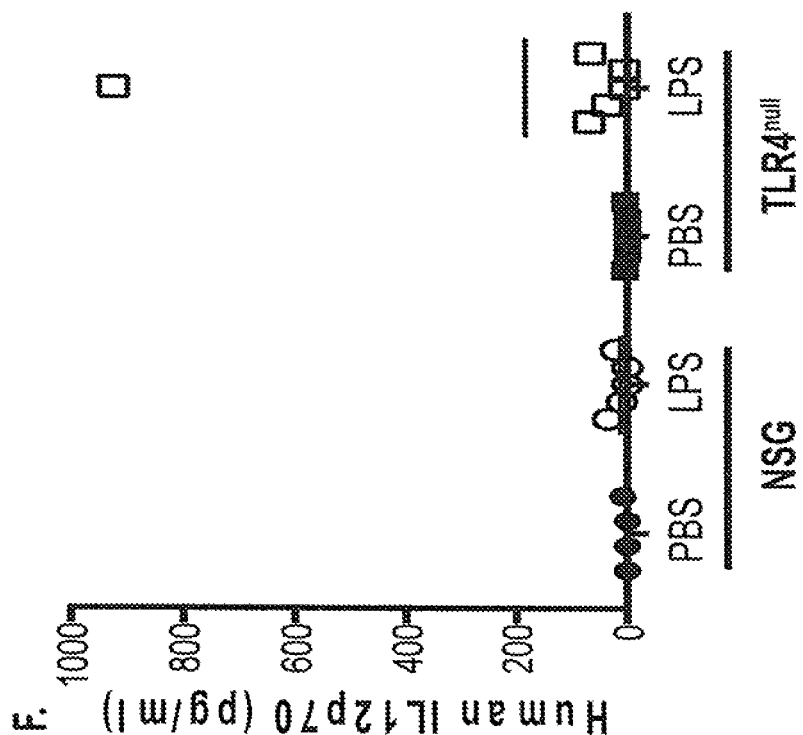
FIG. 7F is a graph showing results of an assay for human IL12p70 in serum samples from HSC-engrafted NSG and NSG-TLR4$^{null}$ mice at 6 hours after LPS or PBS treatment.
Figure 7E:
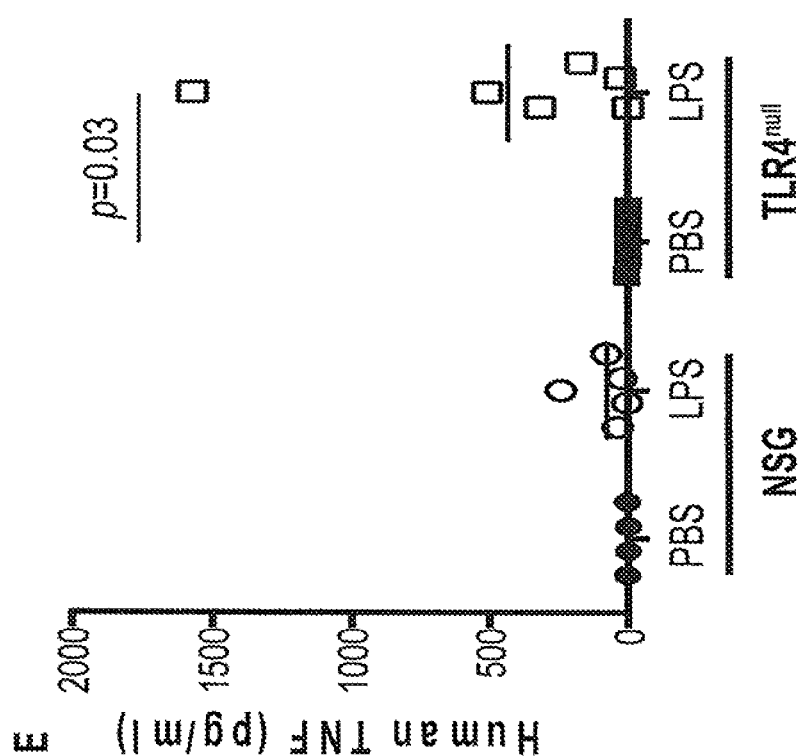
FIG. 7E is a graph showing results of an assay for human TNF in serum samples from HSC-engrafted NSG and NSG-TLR4$^{null}$ mice at 6 hours after LPS or PBS treatment.
Figures 8A, 8B:
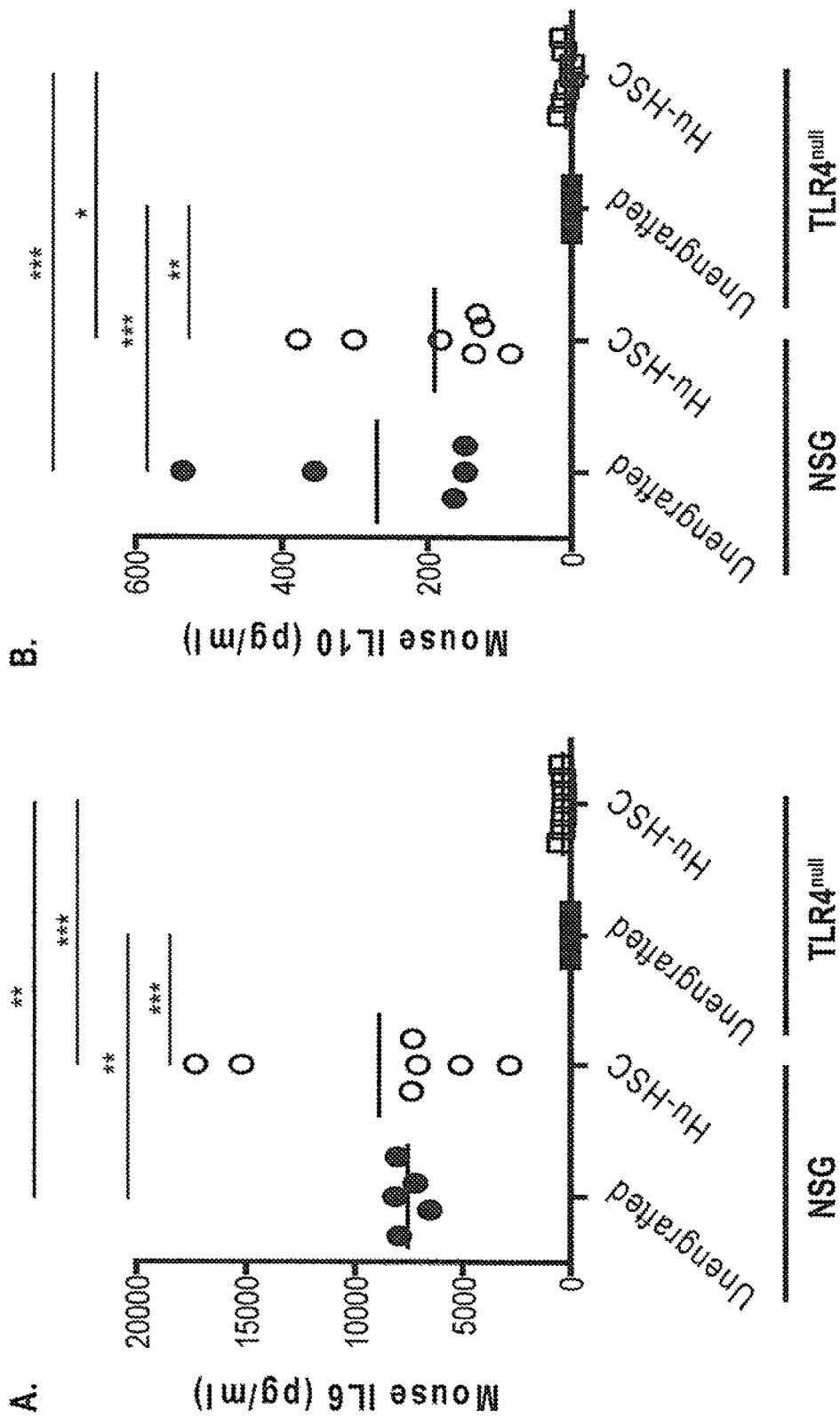
FIG. 8A is a graph showing results of an assay for murine IL6 in serum samples from unengrafted or HSC-engrafted (HuHSC) NSG and NSG-TLR4$^{null}$ mice at 6 hours after LPS or PBS treatment.
FIG. 8B is a graph showing results of an assay for murine IL10 in serum samples from HSC-engrafted NSG and NSG-TLR4$^{null}$ mice at 6 hours after LPS or PBS treatment.

LPS Treatment of HSC-Engrafted NSG-TLR4$^{null}$ Mice Stimulates Production of Human Inflammatory Cytokines in the Absence of a Mouse Cytokine Response Human cytokine production in HSC-engrafted NSG and NSG-TLR4$^{null}$ mice after LPS treatment was compared and results are shown in FIGS. 7A-7F. HSC-engrafted mice were injected IP with PBS or LPS and serum was harvested 6 hours later. The recovered serum samples were tested by CBA for levels of human IL8 (FIG. 7A), human IL1β (FIG. 7B), human IL6 (FIG. 7C), human IL10 (FIG. 7D), human TNF (FIG. 7E) and human IL12p70 (FIG. 7F). Each point in FIGS. 7A-7F represents an individual animal, and the data are from a total of 2 independent experiments. For statistical analysis, the average cytokine levels for LPS treated mice were compared to levels for PBS treated mice. LPS treatment stimulated significant increases in IL8, IL1β and IL6 in both HSC-engrafted NSG and NSG-TLR4$^{null}$ mice. In addition, increased levels of TNF were detected in HSC-engrafted TLR4$^{null}$ mice but not in NSG mice. No significant increases were detected in levels of human IL10 and IL12p70.

It was then determined whether production of human cytokines in HSC-engrafted NSG-TLR4$^{null}$ mice stimulated by LPS would activate murine innate immune cells to produce inflammatory cytokines in a bystander manner. To test this, NSG and NSG-TLR4$^{null}$ mice that were either unmanipulated or engrafted with human HSC were injected IP with 100 μg LPS and serum was collected 6 hours later for cytokine analyses by CBA results of which are shown in FIGS. 8A-8D. Each point in FIGS. 8A-8D represents an individual animal. * p<0.01,  p<0.01, * p<0.001, **** p<0.0001. Mouse IL6 (FIG. 8A), mouse IL10 (FIG. 8B), mouse MCP1 (FIG. 8C) and mouse TNF (FIG. 8D) were detected at significantly higher levels in NSG mice as compared to both unmanipulated or HSC-engrafted NSG-TLR4$^{null}$ mice. The levels of mouse cytokines detected in HSC-engrafted NSG-TLR4$^{null}$ mice treated with LPS were not significantly higher than levels in unmanipulated NSG-TLR4$^{null}$ mice treated with LPS. Overall these results indicate that LPS-induced human inflammatory cytokines in HSC-engrafted NSG-TLR4$^{null}$ mice do not stimulate bystander activation of the mouse innate immune system.

Figures 9A, 9B:
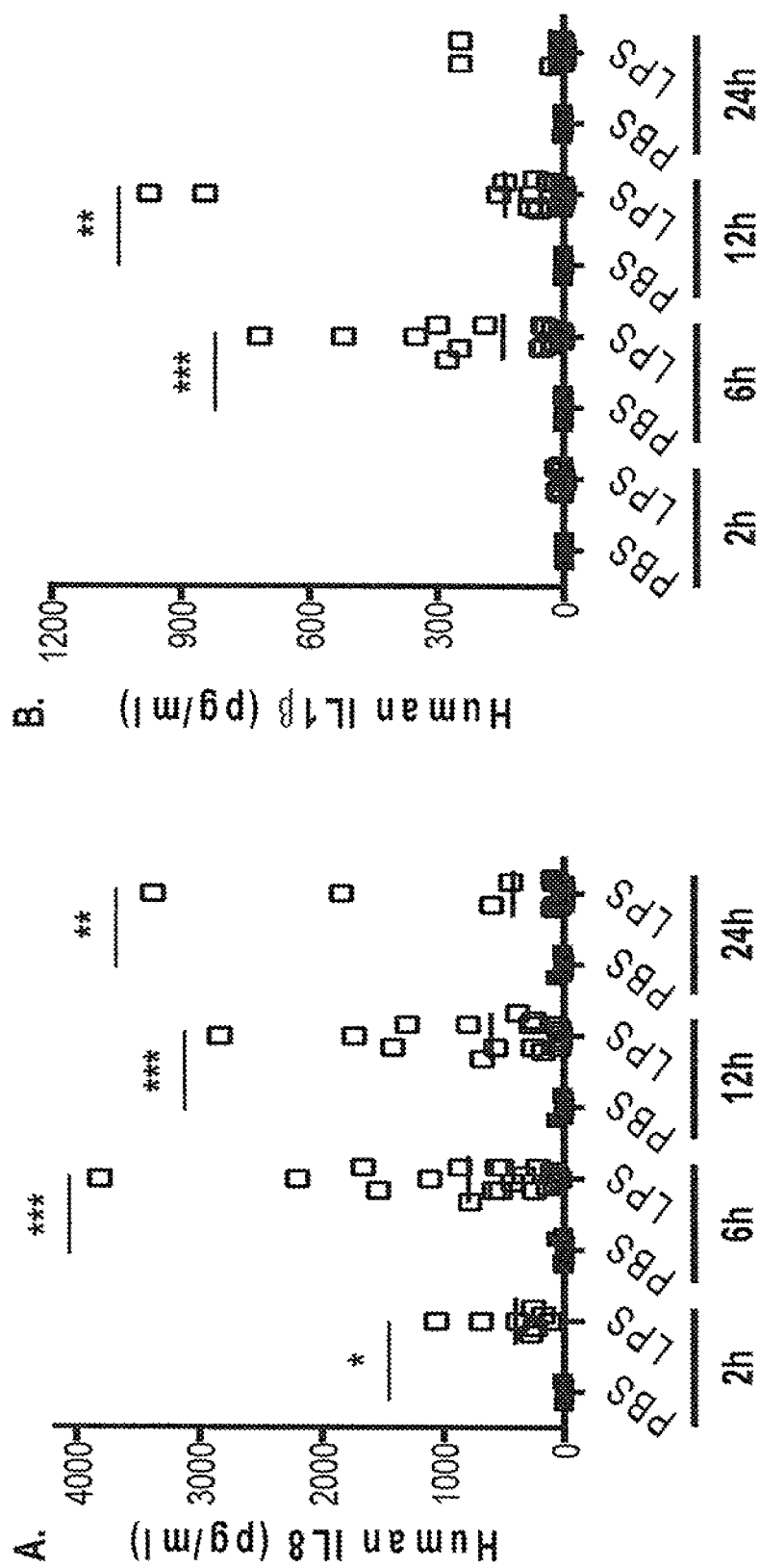
FIG. 9A is a graph showing results of an assay for human IL8 in serum samples from HSC-engrafted NSG and NSG-TLR4$^{null}$ mice at 2, 6, 12 or 24 hours after LPS or PBS treatment.
FIG. 9B is a graph showing results of an assay for human IL1β in serum samples from HSC-engrafted NSG and NSG-TLR4$^{null}$ mice at 6 hours after LPS or PBS treatment.
Figure 9D:
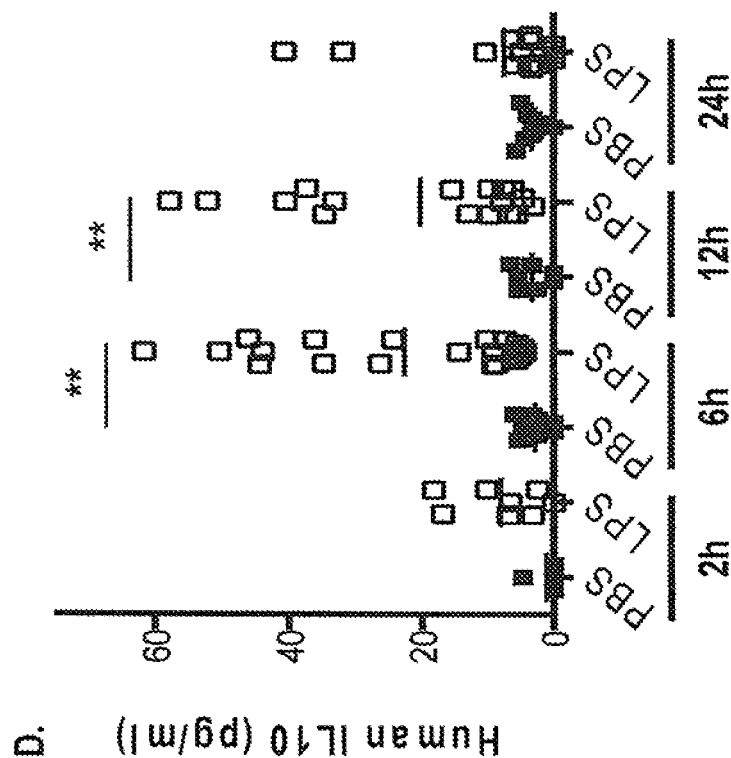
FIG. 9D is a graph showing results of an assay for human IL10 in serum samples from HSC-engrafted NSG and NSG-TLR4$^{null}$ mice at 2, 6, 12 or 24 hours after LPS or PBS treatment.
Figure 9C:
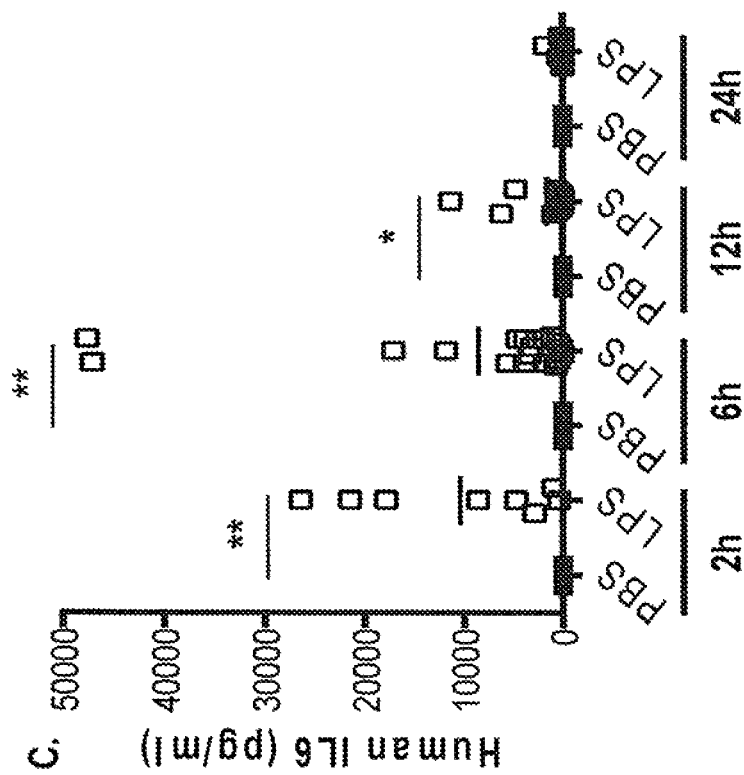
FIG. 9C is a graph showing results of an assay for human IL6 in serum samples from HSC-engrafted NSG and NSG-TLR4$^{null}$ mice at 2, 6, 12 or 24 hours after LPS or PBS treatment.

A kinetic analysis of human cytokine production that was stimulated by LPS treatment of HSC-engrafted NSG-TLR4$^{null}$ mice was performed. HSC-engrafted NSG-TLR4$^{null}$ mice were injected IP with PBS or LPS and serum samples were recovered at 2, 6 12 and 24 hours for quantification by CBA of human IL8, human IL1β, human IL6, human IL10, human TNF and human IL12p70. Results are shown in FIGS. 9A-9F. Each point in FIGS. 9A-9F represents an individual animal, and the data are from a total of 3 independent experiments. For statistical analysis, the average cytokine levels for LPS treated mice were compared to levels for PBS treated mice at each time point; * p<0.05,  p<0.01, * p<0.001. Human IL-8 production was first detectable at 2 hours, peaking at 6 hours and declining by 24 hours (FIG. 9A). Human IL1β was first detectable at 6 hours with the response declining by 12 hours (FIG. 9B). Human IL6 was first detectable at 2 hours with the response declining by 12 hours (FIG. 9C). Human IL10 was first detectable at 6 hours with the response declining by 24 hours (FIG.

Figure 9F:
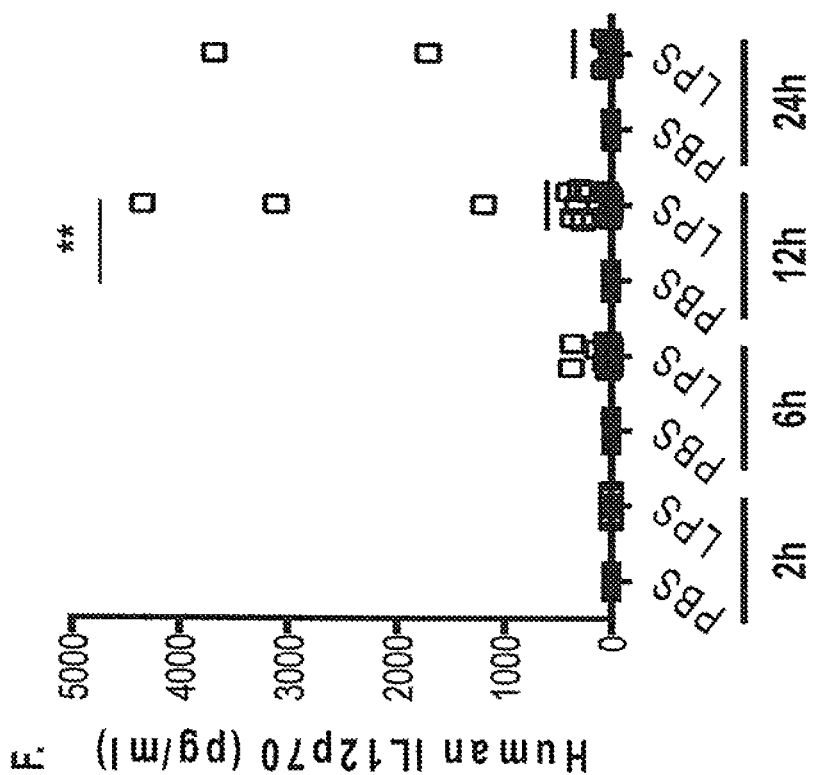
FIG. 9F is a graph showing results of an assay for human IL12p70 in serum samples from HSC-engrafted NSG and NSG-TLR4$^{null}$ mice at 2, 6, 12 or 24 hours after LPS or PBS treatment.
Figure 9E:
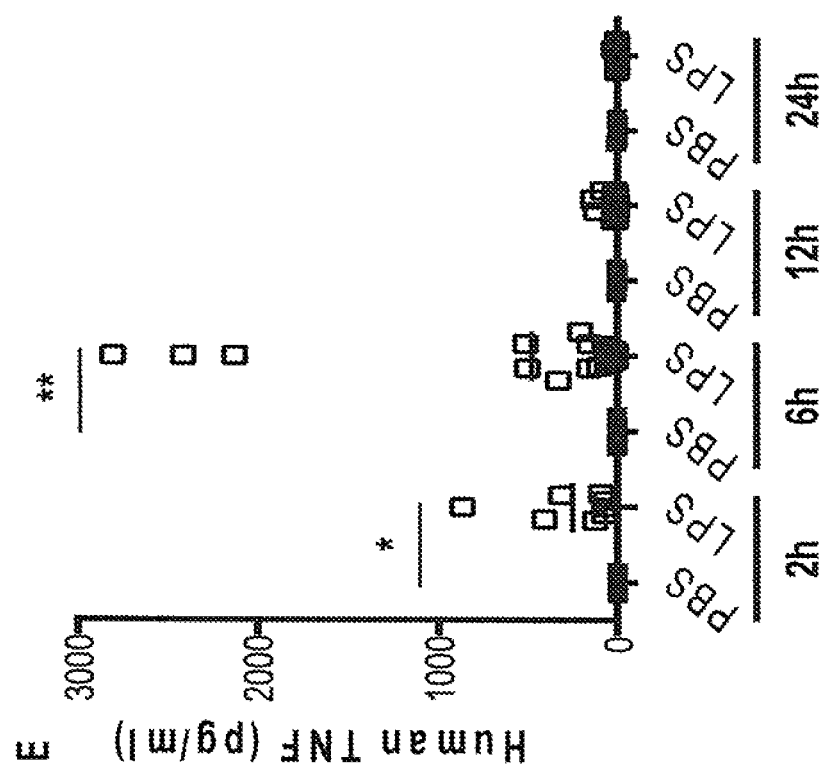
FIG. 9E is a graph showing results of an assay for human TNF in serum samples from HSC-engrafted NSG and NSG-TLR4$^{null}$ mice at 2, 6, 12 or 24 hours after LPS or PBS treatment.

9D). Human TNF was first detectable at 2 hours and the response was not detectable at 12 hours (FIG. 9E). Low levels of human IL-12p70 were detectable at the 12 hour time point (FIG. 9F). Together these data indicate that HSC-engrafted NSG-TLR4$^{null}$ mice can be used to study human-specific cytokine responses to TLR4 agonists.

To determine if the human innate immune system in cord blood HSC-engrafted NSG-TLR4$^{null}$ mice will differentiate between LPS preparations with different levels of TLR4-simulating capacity FISC-engrafted NSG-TLR4$^{null}$ mice were injected IP with PBS or 25 μg of LPS derived from *E. coli* or *Y. pestis*. LPS derived from *Yersinia pestis* (KIM5 strain) cultured at 37° C. has weak TLR4-stimulating capacity with human PBMC as compared to LPS derived from *E. coli*, see, Montminy, Nat Immunol. 2006 October; 7(10): 1066-73, 2006. Blood was collected at 6 hours for human cytokine analysis and at 24 hours to evaluate the activation level of human innate immune cells.

Figures 10A, 10B:
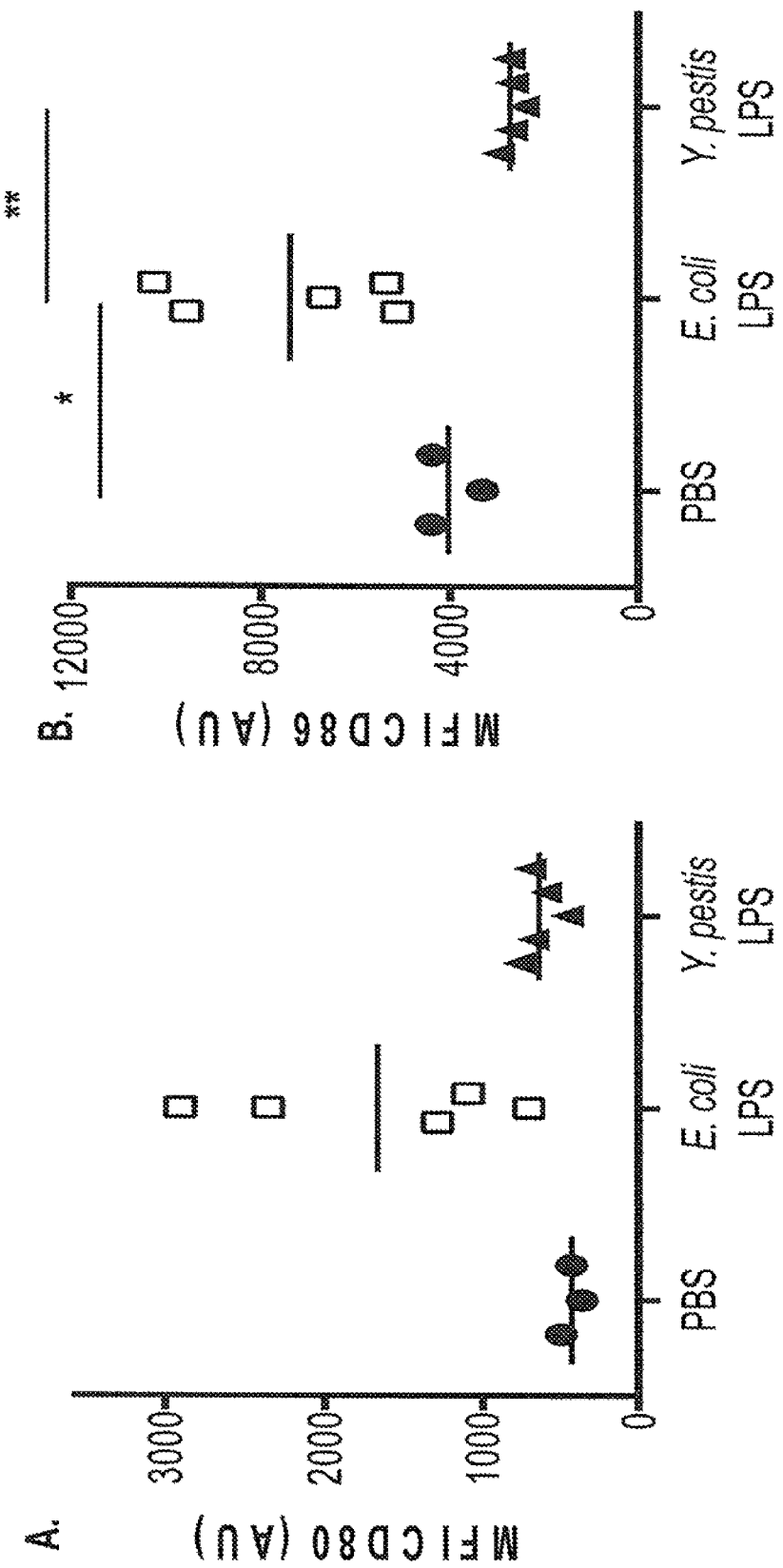
FIGS. 10A-F show that NSG-TLR4$^{null}$ mice engrafted with human HSC show a reduced innate immune response to LPS derived from *Y. pestis*. NSG-TLR4$^{null}$ newborn mice were Rag1tm1Mom Il2rg$^{tm1Wjl}$/SzJ, Shultz L D et al, 2008 Clin Exp Immunol 154(2):270-84 commonly referred to as NRG mice.
Figures 10C, 10D:
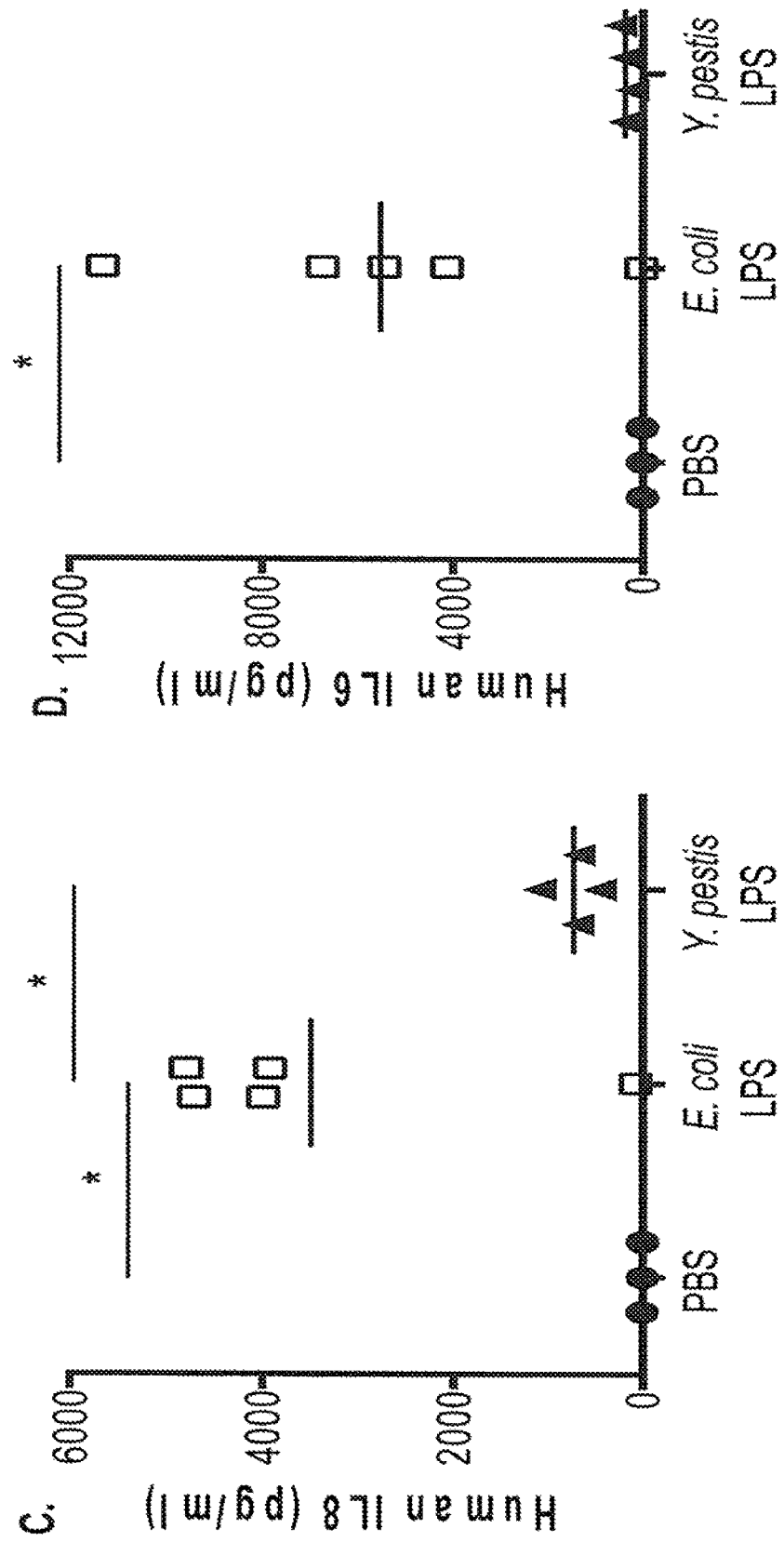
Figures 10E, 10F:
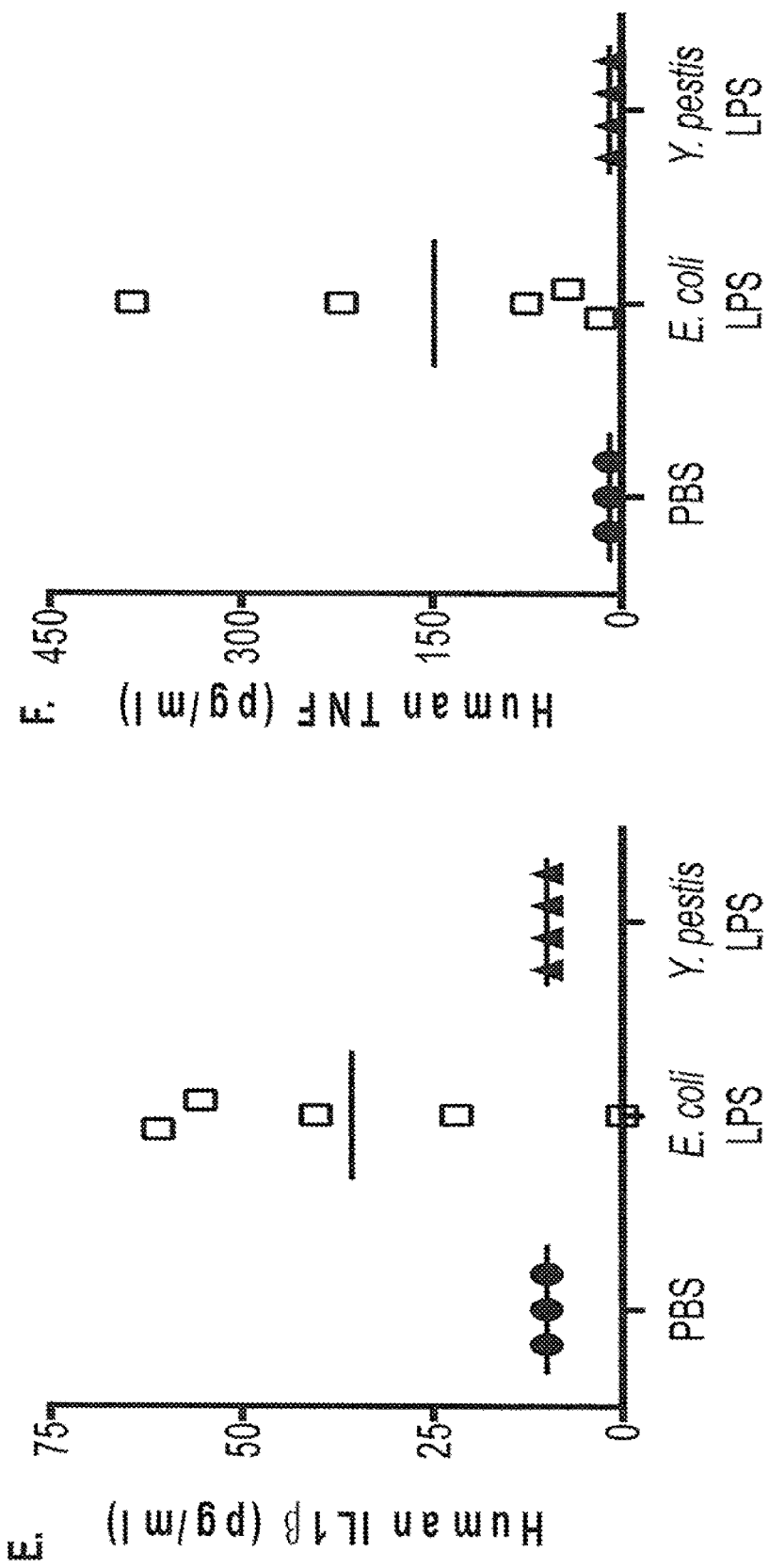

Expression of human CD80 (FIG. 10B) and CD86 (FIG. 10C) was evaluated on CD14+ human monocyte/macrophage from blood of HSC-engrafted NSG-TLR4$^{null}$ mice at 24 hours after LPS injection. Treatment of HSC-engrafted NSG-TLR4$^{null}$ mice with LPS stimulated a significant increase in the expression of CD80 and CD86 on CD14+ monocyte/macrophage (FIGS. 10A, 10B). Serum samples collected from HSC-engrafted NSG-TLR4$^{null}$ mice at 6 hours were analyzed for human cytokine levels. Treatment with LPS derived from *E. coli* stimulated the production of human IL8 (FIG. 10C) and IL6 (FIG. 10D) at levels significantly higher than mice treated with PBS or with LPS derived from *E. coli* or *Y. pestis*. Human IL1β (FIG. 10C) and TNF (FIG. 10D) levels were also higher with *E. coli*-LPS as compared to PBS and *Y. pestis*-LPS, but these differences were not significant. Together these data indicate that human innate immune response in HSC-engrafted NSG-TLR4$^{null}$ mice will reflect the stimulatory capacity of TLR4 agonists in the absence of the confounding effects of the murine host innate immune response to TLR4 agonists.

Any patents or publications mentioned in this specification are incorporated herein by reference to the same extent as if each individual publication is specifically and individually indicated to be incorporated by reference.

The non-human animals, compositions and methods of the present invention described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A genetically modified immunodeficient mouse, wherein the genome of the mouse comprises a homozygous toll-like receptor 4 gene knockout and a homozygous scid mutation, wherein the mouse has an IL2 receptor gamma chain deficiency, wherein the mouse has severe combined immunodeficiency (SCID) characterized by an absence of endogenous T cells and lack of endogenous B cell function, and wherein the mouse is characterized by efficient engraftment of human haematopoietic stem cells providing development of both adaptive and innate human immune cells in the mouse.

2. The genetically modified immunodeficient mouse of claim 1, further comprising xenogeneic haematopoietic stem cells.

3. The genetically modified immunodeficient mouse of claim 1, further comprising human haematopoietic stem cells.

4. The genetically modified immunodeficient mouse of claim 1, further comprising xenogeneic innate immune cells.

5. The genetically modified immunodeficient mouse of claim 1, further comprising human innate immune cells.

6. A method for producing a mouse model system for response of human innate immune cells, comprising:
   providing a genetically modified immunodeficient mouse, wherein the genome of the mouse comprises a homozygous toll-like receptor 4 gene knockout and a homozygous scid mutation, wherein the mouse has an IL2 receptor gamma chain deficiency, wherein the mouse has severe combined immunodeficiency (SCID) characterized by an absence of endogenous T cells and lack of endogenous B cell function, and wherein the mouse is characterized by efficient engraftment of human haematopoietic stem cells providing development of both adaptive and innate human immune cells in the mouse; and
   administering human haematopoietic stem cells to the genetically modified immunodeficient mouse.

7. A method for identifying modulators of a human innate immune system response, comprising:
   providing a genetically modified immunodeficient mouse, wherein the genome of the mouse comprises a homozygous toll-like receptor 4 gene knockout and a homozygous scid mutation, wherein the mouse has an IL2 receptor gamma chain deficiency, wherein the mouse has severe combined immunodeficiency (SCID) characterized by an absence of endogenous T cells and lack of endogenous B cell function, and wherein the mouse is characterized by efficient engraftment of human haematopoietic stem cells providing development of both adaptive and innate human immune cells in the mouse;
   administering human haematopoietic stem cells to the genetically modified immunodeficient mouse, wherein the human haematopoietic stem cells differentiate to produce human innate immune cells in the genetically modified immunodeficient mouse;
   administering an innate immune system stimulator to the mouse;
   administering a test compound to the mouse;
   assaying a response of the human innate immune cells to the stimulator; and
   comparing the response to a standard to determine the effect of the test compound on the response of the human innate immune cells to the stimulator, wherein an effect of the test compound identifies a modulator of the human innate immune system in the mouse.

* * * * *